US009469675B2

(12) United States Patent
Bean et al.

(10) Patent No.: US 9,469,675 B2
(45) Date of Patent: Oct. 18, 2016

(54) ANTI-INFLAMMATORY PROTEINS AND METHODS OF PREPARATION AND USE THEREOF

(75) Inventors: Amanda Bean, Hamilton (NZ); Peter Molan, Hamilton (NZ); Ray Cursons, Hamilton (NZ); Richard Wilkins, Lyttelton (NZ)

(73) Assignee: ManukaMed Limited, Masterton (NZ)

( * ) Notice: Subject to any disclaimer, the term of this patent is extended or adjusted under 35 U.S.C. 154(b) by 230 days.

(21) Appl. No.: 13/997,031

(22) PCT Filed: Dec. 22, 2011

(86) PCT No.: PCT/NZ2011/000271
§ 371 (c)(1),
(2), (4) Date: Feb. 4, 2014

(87) PCT Pub. No.: WO2012/087160
PCT Pub. Date: Jun. 28, 2012

(65) Prior Publication Data
US 2014/0154803 A1    Jun. 5, 2014

(30) Foreign Application Priority Data
Dec. 22, 2010 (NZ) ........................ 590143

(51) Int. Cl.
| C07K 14/435 | (2006.01) |
| G01N 21/64 | (2006.01) |
| G01N 33/15 | (2006.01) |
| G01N 33/68 | (2006.01) |
| A61K 38/00 | (2006.01) |

(52) U.S. Cl.
CPC ......... *C07K 14/43572* (2013.01); *G01N 21/64* (2013.01); *G01N 33/15* (2013.01); *G01N 33/68* (2013.01); *A61K 38/00* (2013.01); *G01N 2333/43565* (2013.01)

(58) Field of Classification Search
None
See application file for complete search history.

(56) References Cited

U.S. PATENT DOCUMENTS

| 7,230,079 B2 | 6/2007 | Okamoto et al. |
| 9,180,219 B2 | 11/2015 | Watson |
| 2006/0159834 A1 | 7/2006 | Shibuya et al. |
| 2008/0292715 A1 | 11/2008 | Snow et al. |
| 2010/0233285 A1 | 9/2010 | Stuart et al. |
| 2012/0269879 A1 | 10/2012 | Watson |
| 2013/0171262 A1 | 7/2013 | Stuart et al. |
| 2015/0337019 A1 | 11/2015 | Johnson et al. |

FOREIGN PATENT DOCUMENTS

| CN | 1980577 A | 6/2007 |
| JP | H11246600 A | 9/1999 |
| JP | 2008-137968 | 6/2008 |
| WO | 2010044042 A1 | 4/2010 |

OTHER PUBLICATIONS

Mavric et al. Mol. Nutr. Food Res. 2008. 52. 483-489.*
Yamawaki et al. Am J Physiol Cell Physiol. 295: C1510-C1517, 2008.*
Mavric et al. Mol Nutr Food Res. 52, 483-489. 2008.*
Prakash et al. Phytotherapy Research. 22, 1511-1519, 2008.*
Adams, C.J. et al., "Isolation of HPLC and characterisation of the bioactive fraction of New Zealand manuka (*Leptospermum scoparium*) honey," Carbohydrate Research, vol. 343(4):651-659 (2008).
Bilikova, Katarina et al., "Towards functional proteomics of minority component of honeybee royal jelly: the effect of post-transitional modifications on the antimicrobial activity of apalbumin2," Proteomics, vol. 9(8):2131-2138 (2009).
Fan, X. et al., "Methylglyoxal-bovine serum albumin stimulates tumor necrosis factor alpha secretion in RAW 264.7 cells through activation of mitogen-activating protein kinase, nuclear factor kappaB and intracellular reactive oxygen species formation," Archives of Biochemistry and Biophysics, vol. 409(2):274-286 (2003).
Simuth, Jozef et al., "Immunochemical approach to detection of adulteration in honey: physiologically active royal jelly protein stimulating TNF-alpha release is a regular component of honey," Journal of Agricultural and Food Chemistry, vol. 52(8):2154-2158 (2004).
Supplementary European Search Report for Application No. 11851351.4, 10 Pages, dated Apr. 9, 2014.
GenBank Accession No. NP_001011579, Major Royal Jelly Protein 1 Precursor [Apis mellifera], 2 pages. (2013).
Majtan, J. et al., "The immunostimulatory effect of the recombinant apalbumin 1-major honeybee royal jelly protein-on TFNalpha release," Int. Immunopharmacol., vol. 6(2):269-278 (2005).
Majtan, Juraj, "Methylglyoxal—A Potential Risk Factor of Manuka Honey in Healing of Diabetic Ulcers," Evidence-Based Complementary and Alternative Medicine, vol. 2011, Article ID 295494, 5 pages (2010).
International Preliminary Report on Patentability and Written Opinion for Application No. PCT/NZ2011/000271, 8 pages, dated Jun. 25, 2013.
International Search Report for Application No. PCT/NZ2011/000271, 4 pages, dated Aug. 22, 2012.
U.S. Appl. No. 12/996,146, filed Apr. 6, 2011, Denis Eric Watson.

(Continued)

*Primary Examiner* — Amber D Steele
*Assistant Examiner* — Schuyler Milton
(74) *Attorney, Agent, or Firm* — Nelson Mullins Riley & Scarborough LLP; Jane E. Remillard, Esq.; Cynthia L. Kanik

(57) ABSTRACT

The present disclosure relates to anti-inflammatory proteins, their uses, methods of preparation and methods of their detection. In particular, the invention relates to major royal jelly proteins modified by methyglyoxal and fragments thereof from manuka honey.

9 Claims, 15 Drawing Sheets

(56) References Cited

OTHER PUBLICATIONS

U.S. Appl. No. 14/025,407, filed Sep. 12, 2013, Denis Eric Watson.
U.S. Appl. No. 12/519,002, filed Dec. 11, 2009, Mark Shane Stuart.
U.S. Appl. No. 13/679,283, filed Nov. 16, 2012, Mark Shane Stuart.
U.S. Appl. No. 14/410,227, filed Dec. 22, 2014, Keryn Johnson.
U.S. Appl. No. 12/996,146, Mar. 13, 2013, Abigail L. Fisher.
U.S. Appl. No. 14/025,407, Nov. 6, 2014, Abigail L. Fisher.
U.S. Appl. No. 14/025,407, Mar. 18, 2015, Abigail L. Fisher.
U.S. Appl. No. 12/519,002, Jun. 21, 2012, Patricia A. Leith.
U.S. Appl. No. 13/679,283, Jul. 17, 2014, Patricia A. Leith.
U.S. Appl. No. 13/679,283, Mar. 11, 2015, Patricia A. Leith.
U.S. Appl. No. 14/807,577, filed Jul. 23, 2015, Denis Eric Watson.
U.S. Appl. No. 13/679,283, Mark Shane Stuart, Sep. 17, 2015.
U.S. Appl. No. 14/025,407, Denis Eric Watson, Jul. 6, 2015.
U.S. Appl. No. 14/410,227, Keryn Johnson, Sep. 25, 2015.
Bilikova, K. et al., "New Criterion for Evaluation of Honey: Quantification of Royal Jelly Protein Apalbumin 1 in Honey by ELISA," J. Agric. Food Chem., vol. 58 (15), pp. 8776-8781 (2010).

\* cited by examiner

SEQUENCE LISTING

```
<160> NUMBER OF SEQ ID NOS: 5

<210> SEQ ID NO 1
<211> LENGTH: 432
<212> TYPE: PRT
<213> ORGANISM: Apis mellifera
<220> FEATURE:
<221> NAME/KEY:
<222> LOCATION: (1)..(432)

<400> SEQUENCE: 1
```

```
Met Thr Arg Leu Phe Met Leu Val Cys Leu Gly Ile Val Cys Gln Gly
1               5                   10                  15

Thr Thr Gly Asn Ile Leu Arg Gly Glu Ser Leu Asn Lys Ser Leu Pro
                20                  25                  30

Ile Leu His Glu Trp Lys Phe Phe Asp Tyr Asp Phe Gly Ser Asp Glu
            35                  40                  45

Arg Arg Gln Asp Ala Ile Leu Ser Gly Glu Tyr Asp Tyr Lys Asn Asn
        50                  55                  60

Tyr Pro Ser Asp Ile Asp Gln Trp His Asp Lys Ile Phe Val Thr Met
65                  70                  75                  80

Leu Arg Tyr Asn Gly Val Pro Ser Ser Leu Asn Val Ile Ser Lys Lys
                85                  90                  95

Val Gly Asp Gly Gly Pro Leu Leu Gln Pro Tyr Pro Asp Trp Ser Phe
                100                 105                 110

Ala Lys Tyr Asp Asp Cys Ser Gly Ile Val Ser Ala Ser Lys Leu Ala
            115                 120                 125

Ile Asp Lys Cys Asp Arg Leu Trp Val Leu Asp Ser Gly Leu Val Asn
130                 135                 140

Asn Thr Gln Pro Met Cys Ser Pro Lys Leu Leu Thr Phe Asp Leu Thr
145                 150                 155                 160

Thr Ser Gln Leu Leu Lys Gln Val Glu Ile Pro His Asp Val Ala Val
                165                 170                 175

Asn Ala Thr Thr Gly Lys Gly Arg Leu Ser Ser Leu Ala Val Gln Ser
            180                 185                 190

Leu Asp Cys Asn Thr Asn Ser Asp Thr Met Val Tyr Ile Ala Asp Glu
        195                 200                 205

Lys Gly Glu Gly Leu Ile Val Tyr His Asn Ser Asp Asp Ser Phe His
210                 215                 220

Arg Leu Thr Ser Asn Thr Phe Asp Tyr Asp Pro Lys Phe Thr Lys Met
225                 230                 235                 240

Thr Ile Asp Gly Glu Ser Tyr Thr Ala Gln Asp Gly Ile Ser Gly Met
                245                 250                 255

Ala Leu Ser Pro Met Thr Asn Asn Leu Tyr Tyr Ser Pro Val Ala Ser
            260                 265                 270

Thr Ser Leu Tyr Tyr Val Asn Thr Glu Gln Phe Arg Thr Ser Asp Tyr
        275                 280                 285

Gln Gln Asn Asp Ile His Tyr Glu Gly Val Gln Asn Ile Leu Asp Thr
        290                 295                 300

Gln Ser Ser Ala Lys Val Val Ser Lys Ser Gly Val Leu Phe Phe Gly
305                 310                 315                 320

Leu Val Gly Asp Ser Ala Leu Gly Cys Trp Asn Glu His Arg Thr Leu
                325                 330                 335

Glu Arg His Asn Ile Arg Thr Val Ala Gln Ser Asp Glu Thr Leu Gln
            340                 345                 350

Met Ile Ala Ser Met Lys Ile Lys Glu Ala Leu Pro His Val Pro Ile
        355                 360                 365

Phe Asp Arg Tyr Ile Asn Arg Glu Tyr Ile Leu Val Leu Ser Asn Lys
370                 375                 380

Met Gln Lys Met Val Asn Asn Asp Phe Asn Phe Asp Asp Val Asn Phe
385                 390                 395                 400

Arg Ile Met Asn Ala Asn Val Asn Glu Leu Ile Leu Asn Thr Arg Cys
                405                 410                 415
```

Glu Asn Pro Asp Asn Asp Arg Thr Pro Phe Lys Ile Ser Ile His Leu
                420                 425                 430

<210> SEQ ID NO 2
<211> LENGTH: 452
<212> TYPE: PRT
<213> ORGANISM: Apis mellifera
<220> FEATURE:
<221> NAME/KEY:
<222> LOCATION: (1)..(452)

<400> SEQUENCE: 2

Met Thr Arg Trp Leu Phe Met Val Ala Cys Leu Gly Ile Ala Cys Gln
1               5                   10                  15

Gly Ala Ile Val Arg Glu Asn Ser Pro Arg Asn Leu Glu Lys Ser Leu
            20                  25                  30

Asn Val Ile His Glu Trp Lys Tyr Phe Asp Tyr Asp Phe Gly Ser Glu
        35                  40                  45

Glu Arg Arg Gln Ala Ala Ile Gln Ser Gly Glu Tyr Asp His Thr Lys
    50                  55                  60

Asn Tyr Pro Phe Asp Val Asp Gln Trp Arg Asp Lys Thr Phe Val Thr
65                  70                  75                  80

Ile Leu Arg Tyr Asp Gly Val Pro Ser Thr Leu Asn Val Ile Ser Gly
                85                  90                  95

Lys Thr Gly Lys Gly Gly Arg Leu Leu Lys Pro Tyr Pro Asp Trp Ser
            100                 105                 110

Phe Ala Glu Phe Lys Asp Cys Ser Lys Ile Val Ser Ala Phe Lys Ile
        115                 120                 125

Ala Ile Asp Lys Phe Asp Arg Leu Trp Val Leu Asp Ser Gly Leu Val
    130                 135                 140

Asn Arg Thr Val Pro Val Cys Ala Pro Lys Leu His Val Phe Asp Leu
145                 150                 155                 160

Lys Thr Ser Asn His Leu Lys Gln Ile Glu Ile Pro His Asp Ile Ala
                165                 170                 175

Val Asn Ala Thr Thr Gly Lys Gly Gly Leu Val Ser Leu Ala Val Gln
            180                 185                 190

Ala Ile Asp Leu Ala Asn Thr Leu Val Tyr Met Ala Asp His Lys Gly
        195                 200                 205

Asp Ala Leu Ile Val Tyr Gln Asn Ala Asp Ser Phe His Arg Leu
    210                 215                 220

Thr Ser Asn Thr Phe Asp Tyr Asp Pro Arg Tyr Ala Lys Met Thr Ile
225                 230                 235                 240

Asp Gly Glu Ser Phe Thr Leu Lys Asn Gly Ile Cys Gly Met Ala Leu
                245                 250                 255

Ser Pro Val Thr Asn Asn Leu Tyr Tyr Ser Pro Leu Ala Ser His Gly
            260                 265                 270

Leu Tyr Tyr Val Asn Thr Ala Pro Phe Met Lys Ser Gln Phe Gly Glu
        275                 280                 285

Asn Asn Val Gln Tyr Gln Gly Ser Glu Asp Ile Leu Asn Thr Gln Ser
    290                 295                 300

Leu Ala Lys Ala Val Ser Lys Asn Gly Val Leu Phe Val Gly Leu Val
305                 310                 315                 320

Gly Asn Ser Ala Val Gly Cys Trp Asn Glu His Gln Ser Leu Gln Arg
                325                 330                 335

Gln Asn Leu Glu Met Val Ala Gln Asn Asp Arg Thr Leu Gln Met Ile
            340                 345                 350

```
Ala Gly Met Lys Ile Lys Glu Glu Leu Pro His Phe Val Gly Ser Asn
        355                 360                 365

Lys Pro Val Lys Asp Glu Tyr Met Leu Val Leu Ser Asn Arg Met Gln
    370                 375                 380

Lys Ile Val Asn Asp Asp Phe Asn Phe Asp Val Asn Phe Arg Ile
385                 390                 395                 400

Leu Gly Ala Asn Val Lys Glu Leu Ile Arg Asn Thr His Cys Val Asn
                405                 410                 415

Asn Asn Gln Asn Asp Asn Ile Gln Asn Thr Asn Asn Gln Asn Asp Asn
            420                 425                 430

Asn Gln Lys Asn Asn Lys Lys Asn Ala Asn Asn Gln Lys Asn Asn Asn
            435                 440                 445

Gln Asn Asp Asn
    450
```

<210> SEQ ID NO 3
<211> LENGTH: 544
<212> TYPE: PRT
<213> ORGANISM: Apis mellifera
<220> FEATURE:
<221> NAME/KEY:
<222> LOCATION: (1)..(544)
<220> FEATURE:
<221> NAME/KEY:
<222> LOCATION: (1)..(544)

<400> SEQUENCE: 3

```
Met Thr Lys Trp Leu Leu Leu Val Val Cys Leu Gly Ile Ala Cys Gln
1               5                   10                  15

Asp Val Thr Ser Ala Ala Val Asn His Gln Arg Lys Ser Ala Asn Asn
                20                  25                  30

Leu Ala His Ser Met Lys Val Ile Tyr Glu Trp Lys His Ile Asp Phe
            35                  40                  45

Asp Phe Gly Ser Asp Glu Arg Arg Asp Ala Ala Ile Lys Ser Gly Glu
    50                  55                  60

Phe Asp His Thr Lys Asn Tyr Pro Phe Asp Val Asp Arg Trp Arg Asp
65                  70                  75                  80

Lys Thr Phe Val Thr Ile Glu Arg Asn Asn Gly Val Pro Ser Ser Leu
                85                  90                  95

Asn Val Val Thr Asn Lys Lys Gly Lys Gly Pro Leu Leu Arg Pro
                100                 105                 110

Tyr Pro Asp Trp Ser Phe Ala Lys Tyr Glu Asp Cys Ser Gly Ile Val
            115                 120                 125

Ser Ala Phe Lys Ile Ala Val Asp Lys Phe Asp Arg Leu Trp Val Leu
    130                 135                 140

Asp Ser Gly Leu Val Asn Asn Asn Gln Pro Met Cys Ser Pro Lys Leu
145                 150                 155                 160

Leu Thr Phe Asp Leu Lys Thr Ser Lys Leu Val Lys Gln Val Glu Ile
                165                 170                 175

Pro His Asn Ile Ala Val Asn Ala Thr Thr Gly Met Gly Glu Leu Val
            180                 185                 190

Ser Leu Ala Val Gln Ala Ile Asp Arg Thr Asn Thr Met Val Tyr Ile
    195                 200                 205

Ala Asp Glu Lys Gly Glu Gly Leu Ile Met Tyr Gln Asn Ser Asp Asp
210                 215                 220
```

Ser Phe His Arg Leu Thr Ser Asn Thr Phe Asp Tyr Asp Pro Arg Tyr
225                 230                 235                 240

Thr Lys Leu Thr Val Ala Gly Glu Ser Phe Thr Val Lys Asn Gly Ile
            245                 250                 255

Tyr Gly Ile Ala Leu Ser Pro Val Thr Asn Asn Leu Tyr Tyr Ser Pro
        260                 265                 270

Leu Leu Ser His Gly Leu Tyr Tyr Val Asp Thr Glu Gln Phe Ser Asn
    275                 280                 285

Pro Gln Tyr Glu Glu Asn Asn Val Gln Tyr Gly Ser Gln Asp Ile
290                 295                 300

Leu Asn Thr Gln Ser Phe Gly Lys Val Val Ser Lys Asn Gly Val Leu
305                 310                 315                 320

Phe Leu Gly Leu Val Gly Asn Ser Gly Ile Ala Cys Val Asn Glu His
                325                 330                 335

Gln Val Leu Gln Arg Glu Ser Phe Asp Val Val Ala Gln Asn Glu Glu
                340                 345                 350

Thr Leu Gln Met Ile Val Ser Met Lys Ile Met Glu Asn Leu Pro Gln
            355                 360                 365

Ser Gly Arg Ile Asn Asp Pro Glu Gly Asn Glu Tyr Met Leu Ala Leu
370                 375                 380

Ser Asn Arg Met Gln Lys Ile Ile Asn Asn Asp Phe Asn Phe Asn Asp
385                 390                 395                 400

Val Asn Phe Arg Ile Leu Gly Ala Asn Val Asp Asp Leu Met Arg Asn
                405                 410                 415

Thr Arg Cys Gly Arg Tyr His Asn Gln Asn Ala Gly Asn Gln Asn Ala
            420                 425                 430

Asp Asn Gln Asn Ala Asp Asn Gln Asn Ala Asn Gln Asn Ala Asp
        435                 440                 445

Asn Gln Asn Ala Asn Lys Gln Asn Gly Asn Arg Gln Asn Asp Asn Arg
    450                 455                 460

Gln Asn Asp Asn Lys Gln Asn Gly Asn Arg Gln Asn Asp Asn Lys Gln
465                 470                 475                 480

Asn Gly Asn Arg Gln Asn Asp Asn Lys Gln Asn Gly Asn Arg Gln Asn
                485                 490                 495

Gly Asn Lys Gln Asn Asp Asn Lys Gln Asn Gly Asn Arg Gln Asn Asp
            500                 505                 510

Asn Lys Arg Asn Gly Asn Arg Gln Asn Asp Asn Gln Asn Gln Asn
    515                 520                 525

Asp Asn Asn Arg Asn Asp Asn Gln Val His His Ser Ser Lys Leu His
530                 535                 540

<210> SEQ ID NO 4
<211> LENGTH: 464
<212> TYPE: PRT
<213> ORGANISM: Apis mellifera
<220> FEATURE:
<221> NAME/KEY:
<222> LOCATION: (1)..(464)

<400> SEQUENCE: 4

Met Thr Lys Trp Leu Leu Leu Met Val Cys Leu Gly Ile Ala Cys Gln
1               5                   10                  15

Asn Ile Arg Gly Gly Val Val Arg Glu Asn Ser Ser Gly Lys Asn Leu
            20                  25                  30

Thr Asn Thr Leu Asn Val Ile His Lys Trp Lys Tyr Leu Asp Tyr Asp
        35                  40                  45

```
Phe Asp Asn Asp Glu Arg Arg Gln Ala Ala Ile Gln Ser Gly Glu Tyr
 50                  55                  60

Asp Arg Thr Lys Asn Tyr Pro Leu Asp Val Asp Gln Trp His Asn Lys
 65                  70                  75                  80

Thr Phe Leu Ala Val Ile Arg Tyr Asn Gly Val Pro Ser Ser Leu Asn
                 85                  90                  95

Val Val Ser Asp Lys Thr Gly Asn Gly Gly Arg Leu Leu Gln Pro Tyr
                100                 105                 110

Pro Asp Trp Ser Phe Ala Lys Tyr Glu Asp Cys Ser Gly Ile Val Ser
            115                 120                 125

Ala His Lys Ile Ala Ile Asp Glu Tyr Glu Arg Leu Trp Val Leu Asp
        130                 135                 140

Ser Gly Leu Val Asn Asn Thr Gln Pro Met Cys Ser Pro Lys Leu Phe
145                 150                 155                 160

Ala Phe Asp Leu Asn Thr Ser Gln Leu Leu Lys Gln Val Glu Ile Pro
                165                 170                 175

His Asp Val Ala Thr Thr Gly Lys Gly Glu Leu Val Ser Leu Thr Val
            180                 185                 190

Gln Ala Met Asp Ser Thr Asn Thr Met Val Tyr Met Val Asp Asn Lys
        195                 200                 205

Asn Thr Leu Ile Ile Tyr Gln Asn Ala Asp Asp Ser Phe His Arg Leu
    210                 215                 220

Ser Ser His Thr Leu Asn His Asn Ser Asp Lys Met Ser Asp Gln Gln
225                 230                 235                 240

Glu Asn Leu Thr Leu Lys Glu Val Asp Asn Lys Val Tyr Gly Met Ala
                245                 250                 255

Leu Ser Pro Val Thr His Asn Leu Tyr Tyr Asn Ser Pro Ser Ser Glu
            260                 265                 270

Asn Leu Tyr Tyr Val Asn Thr Glu Ser Leu Met Lys Ser Glu Asn Gln
        275                 280                 285

Gly Asn Asp Val Gln Tyr Glu Arg Val Gln Asp Val Phe Asp Ser Gln
    290                 295                 300

Leu Thr Val Lys Ala Val Ser Lys Asn Gly Val Leu Leu Phe Gly Leu
305                 310                 315                 320

Ala Asn Asn Thr Leu Ser Cys Trp Asn Glu His Gln Ser Leu Asp Arg
                325                 330                 335

Gln Asn Ile Asp Val Val Ala Arg Asn Glu Asp Thr Leu Gln Met Val
            340                 345                 350

Val Ser Met Lys Ile Lys Gln Asn Val Pro Gln Ser Gly Arg Val Asn
        355                 360                 365

Asn Thr Gln Arg Asn Glu Tyr Leu Leu Ala Leu Ser Asp Arg Asn Gln
    370                 375                 380

Asn Val Leu Asn Asn Asp Leu Asn Leu Glu His Val Asn Phe Gln Ile
385                 390                 395                 400

Leu Gly Ala Asn Val Asn Asp Leu Ile Arg Asn Ser Arg Cys Ala Asn
                405                 410                 415

Phe Asp Asn Gln Asp Asn Asn His Tyr Asn His Asn His Asn Gln Ala
            420                 425                 430

Arg His Ser Ser Lys Ser Asp Asn Gln Asn Asn Gln His Asn Asp
        435                 440                 445

Gln Ala His His Ser Ser Lys Ser Asn Asn Arg His Asn Asn Asn Asp
    450                 455                 460
```

```
<210> SEQ ID NO 5
<211> LENGTH: 598
<212> TYPE: PRT
<213> ORGANISM: Apis mellifera
<220> FEATURE:
<221> NAME/KEY:
<222> LOCATION: (1)..(598)

<400> SEQUENCE: 5

Met Thr Thr Trp Leu Leu Leu Val Val Cys Leu Gly Ile Ala Cys Gln
1               5                   10                  15

Gly Ile Thr Ser Val Thr Val Arg Glu Asn Ser Pro Arg Lys Leu Ala
            20                  25                  30

Asn Ser Met Asn Val Ile His Glu Trp Lys Tyr Leu Asp Tyr Asp Phe
        35                  40                  45

Gly Ser Asp Glu Arg Arg Gln Ala Ala Met Gln Ser Gly Glu Tyr Asp
    50                  55                  60

His Thr Lys Asn Tyr Pro Phe Asp Val Asp Gln Trp Arg Gly Met Thr
65                  70                  75                  80

Phe Val Thr Val Pro Arg Tyr Lys Gly Val Pro Ser Ser Leu Asn Val
                85                  90                  95

Ile Ser Glu Lys Ile Gly Asn Gly Gly Arg Leu Leu Gln Pro Tyr Pro
            100                 105                 110

Asp Trp Ser Trp Ala Asn Tyr Lys Asp Cys Ser Gly Ile Val Ser Ala
        115                 120                 125

Tyr Lys Ile Ala Ile Asp Lys Phe Asp Arg Leu Trp Ile Leu Asp Ser
    130                 135                 140

Gly Ile Ile Asn Asn Thr Gln Pro Met Cys Ser Pro Lys Leu His Val
145                 150                 155                 160

Phe Asp Leu Asn Thr Ser His Gln Leu Lys Gln Val Val Met Pro His
                165                 170                 175

Asp Ile Ala Val Asn Ala Ser Thr Gly Asn Gly Gly Leu Val Ser Leu
            180                 185                 190

Val Val Gln Ala Met Asp Pro Val Asn Thr Ile Val Tyr Met Ala Asp
        195                 200                 205

Asp Lys Gly Asp Ala Leu Ile Val Tyr Gln Asn Ser Asp Glu Ser Phe
    210                 215                 220

His Arg Leu Thr Ser Asn Thr Phe Asp Tyr Asp Pro Lys Tyr Ile Lys
225                 230                 235                 240

Met Met Asp Ala Gly Glu Ser Phe Thr Ala Gln Asp Gly Ile Phe Gly
                245                 250                 255

Met Ala Leu Ser Pro Met Thr Asn Asn Leu Tyr Tyr Ser Pro Leu Ser
            260                 265                 270

Ser Arg Ser Leu Tyr Tyr Val Asn Thr Lys Pro Phe Met Lys Ser Glu
        275                 280                 285

Tyr Gly Ala Asn Asn Val Gln Tyr Gln Gly Val Gln Asp Ile Phe Asn
    290                 295                 300

Thr Glu Ser Ile Ala Lys Ile Met Ser Lys Asn Gly Val Leu Phe Phe
305                 310                 315                 320

Gly Leu Met Asn Asn Ser Ala Ile Gly Cys Trp Asn Glu His Gln Pro
                325                 330                 335

Leu Gln Arg Glu Asn Met Asp Met Val Ala Gln Asn Glu Glu Thr Leu
            340                 345                 350

Gln Thr Val Val Ala Met Lys Met Met His Leu Pro Gln Ser Asn Lys
        355                 360                 365
```

```
Met Asn Arg Met His Arg Met Asn Arg Val Asn Arg Val Asn Arg Met
    370             375             380
Asp Arg Met Asp Arg Ile Asp Arg Met Asp Arg Met Asp Arg Met Asp
385             390             395             400
Thr Met Asp Thr Met Asp Arg Ile Asp Arg Met Asp Arg Met Asp Arg
            405             410             415
Ile Asp Arg Ile Asp Arg Met His Thr Met Asp Thr Met Asp Thr Met
            420             425             430
Asp Arg Thr Asp Lys Met Ser Ser Met Asp Arg Met Asp Arg Met Asp
            435             440             445
Arg Val Asp Arg Met Asp Thr Met Asp Arg Thr Asp Lys Met Ser Ser
    450             455             460
Met Asp Arg Met Asp Arg Met Asp Arg Val Asp Thr Met Asp Thr Met
465             470             475             480
Asp Thr Met Asp Arg Met Asp Arg Met Asp Arg Met Asp Arg Met Asp
            485             490             495
Arg Met Asp Arg Met Asp Thr Met Asp Arg Thr Asp Lys Met Ser Arg
            500             505             510
Ile Asp Arg Met Asp Lys Ile Asp Arg Met Asp Arg Met Asp Arg Thr
            515             520             525
Asn Arg Met Asp Arg Met Asn Arg Met Asn Arg Gln Met Asn Glu Tyr
    530             535             540
Met Met Ala Leu Ser Met Lys Leu Gln Lys Phe Ile Asn Asn Asp Tyr
545             550             555             560
Asn Phe Asn Glu Val Asn Phe Arg Ile Leu Gly Ala Asn Val Asn Asp
            565             570             575
Leu Ile Met Asn Thr Arg Cys Ala Asn Ser Asp Asn Gln Asn Asn Asn
            580             585             590
Gln Asn Lys His Asn Asn
    595
```

ANTI-INFLAMMATORY PROTEINS AND METHODS OF PREPARATION AND USE THEREOF

RELATED APPLICATIONS

This application is a 35 U.S.C. 371 national stage filing of International Application No. PCT/NZ2011/000271, filed Dec. 22, 2011, which claims priority to New Zealand Patent Application No. 590143, filed Dec. 22, 2010. The contents of the aforementioned applications are hereby incorporated by reference.

SEQUENCE LISTING

This instant application contains a Sequence Listing which has been submitted in ASCII format via EFS-Web and is hereby incorporated by reference in its entirety. Said ASCII copy, created on Feb. 4, 2014, is named WSJ_005US_Sequence_listing.txt and is 22,208 bytes in size.

BACKGROUND

1. Field

The present disclosure relates to anti-inflammatory proteins, their uses, and methods of their detection.

2. Related Art

Honey has been used for centuries by cultures through the world for its multiple health benefits. Two of the most important health benefits of honey are its anti-bacterial and anti-inflammatory properties. Manuka honey, which is produced by bees that collect nectar from *Leptospermum scoparium*, a plant native to New Zealand and southern Australia, has been identified as being a variety of honey that exhibits particularly effective anti-bacterial and anti-inflammatory properties.

Recently, it was discovered that the chemical, methylglyoxal (MGO/2-oxopropanal), is a major component of the anti-bacterial activity of manuka honey. Manuka honey samples that contain greater concentrations of MGO have a higher amount of anti-bacterial activity as compared to honey samples with lower concentrations of MGO. MGO is believed to confer antibacterial properties on honey because MGO is a highly chemically reactive compound, and MGO can readily react with cellular molecules. The chemical reactions between MGO and cellular molecules in bacteria damage molecules that are important for bacterial viability, and thereby MGO functions as an antibacterial agent.

The presence of high levels of MGO in the honey is a feature that distinguishes manuka honey from other varieties of honey. While most varieties of honey exhibit some anti-bacterial activity, the anti-bacterial activity in most varieties of honey is primarily a result of the presence of hydrogen peroxide in the honey. Manuka honey, in contrast, exhibits anti-bacterial activity primarily because of the presence of MGO in the honey.

In 2004, Kohno et. al. examined the anti-inflammatory effects or actions of royal jelly at a cytokine level. The study results suggest that royal jelly has anti-inflammatory actions brought about by an inhibition of the proinflammatory cytokine production, such as TNF-α, IL-6 and IL-1, by activated macrophages. The study further suggested that the active fractions or components from the royal jelly were between 5 kDa and 30 kDa molecular weights. This study perhaps explains why most honeys have a weak anti-inflammatory effect because of the royal jelly proteins that occur in honey.

While multiple mechanisms of action of the anti-bacterial activity of manuka honey are understood, the mechanisms whereby manuka honey functions as an anti-inflammatory agent have remained unknown. There is a need to develop anti-inflammatory agents based on honey, because many anti-inflammatory agents currently available have major drawbacks to their use. For example, COX-2 inhibitors, a form of non-steroidal anti-inflammatory drug (NSAID), may increase the risk of heart attack and stroke in patients, and aspirin may increase the risk of gastrointestinal bleeding. Additionally, corticosteroids are reported to inhibit the growth of epithelial cells and NSAID's are reported as being cytotoxic so both of these classes of anti-inflammatory agents are unsuitable for use in wound care. Anti-inflammatory agents derived from honey may have fewer toxic side effects in one or more areas than drugs currently available, and may also offer different possible uses than anti-inflammatory drugs currently available.

In addition to the need for the development of anti-inflammatory drugs based on honey, there is also a need to develop a simple method to test the anti-inflammatory characteristics of a sample of honey. This disclosure addresses both of these and other unmet needs.

The inventors have identified a modified apalbumin of approximately 55-75 kDa from Manuka honey that results from the high levels of methylglyoxal found in Manuka honey. The inventors have identified that the modified apalbumin has significantly greater anti-inflammatory properties than an unmodified apalbumin.

SUMMARY

Described herein is an apalbumin protein chemically modified by methylglyoxal (MGO) and identified in honey that exhibits a significantly enhanced anti-inflammatory effect. In one aspect, there is provided an isolated apalbumin protein or fragment thereof, which has been chemically modified by methylglyoxal (MGO). In another embodiment the protein is a modified apalbumin 1 (Apa1/MRJP) protein or a fragment thereof. In a further embodiment the modified apalbumin protein or fragment thereof is isolated from manuka honey.

In another embodiment the protein or fragment thereof has at least 17 amino acid residues modified by MGO, or between 17 and 32 amino acid residues modified by MGO or about 32 amino acid residues modified by MGO. In another embodiment the amino acid residues that are modified are either one or more lysine or arginine residues.

In another aspect, there is provided a composition comprising the isolated MGO-modified apalbumin protein or fragment thereof.

In a further aspect, there is provided an isolated MGO-modified apalbumin protein or fragment thereof that has "anti-inflammatory capacity" comprising at least 75%, 85%, 90%, 91%, 92%, 93%, 94%, 95%, 96%, 97%, 98%, 99% or 100% sequence identity an amino acid sequence to the amino acid sequence set forth in SEQ ID NO 1. In one embodiment the isolated, MGO-modified apalbumin protein or fragment thereof is isolated from manuka honey.

In a further aspect, there is provided a method of reducing inflammation in a cellular tissue, comprising the step of contacting a composition including an isolated, MGO-modified apalbumin protein as defined above to the cellular tissue.

In another aspect, there is provided (i) a method of reducing the rate of phagocytosis by immune system cells, or (ii) a method of inhibiting the receptors for phagocytosis on immune system cells comprising the step of administering the composition of an isolated, MGO-modified apalbumin protein as defined above to immune system cells.

In another embodiment there is provided a method of producing an anti-inflammatory molecule by modifying royal jelly, the method including the step of reacting royal jelly with at least 0.01% MGO, or 0.5% MGO or 1.0% MGO. The method may further include the step of isolating the MGO modified apalbumin (MRJP1) protein from the royal jelly product.

In another aspect there is provided a method of identifying (i) the anti-inflammatory capacity or (ii) MGO-modified apalbumin concentration of a sample of honey, comprising the steps of:
  a) assaying the fluorescence of the honey sample, and
  b) correlating the measure of fluorescence of the honey sample with the anti-inflammatory capacity of the honey sample, by comparing the measure of fluorescence of a sample of honey and the anti-inflammatory capacity of one or more samples of honey with previously measured capacity to inhibit phagocytosis.

In one embodiment the MGO-modified apalbumin is a modified apalbumin 1 protein.

In one embodiment the method is used to enable a bee keeper to determine the right time to harvest honey from a hive in order to obtain a honey sample containing a desired anti-inflammatory capacity or MGO-modified apalbumin content.

In a further embodiment the method is used to enable a honey producer to determine a desired length of time to store honey, in order to obtain a honey sample with a desired anti-inflammatory capacity and MGO-modified apalbumin content.

A method of increasing the anti-inflammatory and fluorescence characteristics of one or more apalbumin/(MRJP) proteins, by chemically treating with MGO.

A method of increasing the anti-inflammatory capacity and MGO-modified apalbumin protein content of a sample of honey, comprising the step of adding MGO or a MGO-precursor molecule to a honey sample.

In another embodiment there is provided a method of increasing the anti-inflammatory capacity of one or more apalbumin proteins, by chemically treating with MGO, formaldehyde, glyoxal and/or glutaraldehyde.

In another embodiment there is provided a method of increasing the anti-inflammatory capacity of one or more apalbumin proteins, by chemically treating with MGO, glyoxal and/or glutaraldehyde.

The foregoing brief summary broadly describes the features and technical advantages of certain embodiments of the present invention. Further technical advantages will be described in the detailed description of the invention and Examples that follows. Novel features which are believed to be characteristic of the invention will be better understood from the detailed description of the invention when considered in connection with any accompanying figures and examples. However, the figures and examples provided herein are intended to help illustrate the invention or assist with developing an understanding of the invention, and are not intended to limit the invention's scope.

DETAILED DESCRIPTION

Figure 1:
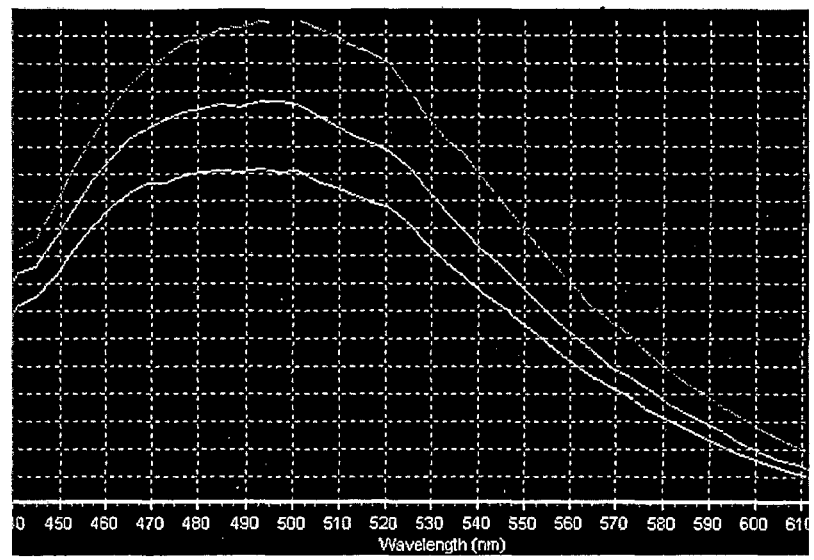
FIG. 1 depicts (a) the fluorescence emission spectra of a 10% solution of a manuka honey with high fluorescence, and (b) a solution of MGO-modified bovine serum albumin prepared by incubating 10 mg/ml bovine serum albumin in water with 400 µg/ml MGO.
Figure 1:
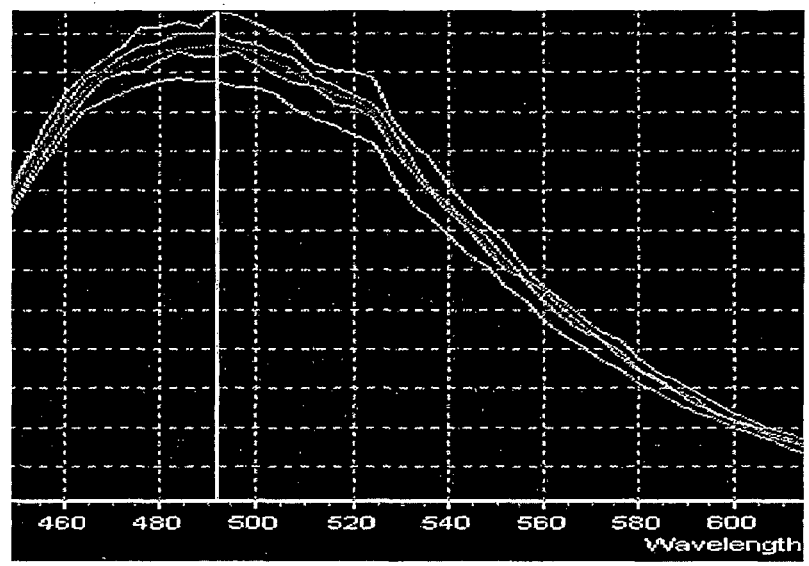

The following description sets forth numerous exemplary configurations, parameters, and the like. It should be recognized, however, that such description is not intended as a limitation on the scope of the present invention, but is instead provided as a description of exemplary embodiments.

DEFINITIONS

An apalbumin protein is a glycoprotein. There are a number of apalbumins that are found in honey and in royal jelly. The major apalbumin found in honey is Apalbumin 1 (Apa1) also known as Major Royal Jelly Protein 1 (MRJP1). While the specification focuses on the major apalbumin found in honey, it is to be appreciated that the other apalbumins found in honey may also exhibit similar modification potential and similar anti-inflammatory capacity because they are all glycoproteins with a high mannose type of glycosylation as reported in 2000 by Kimura et. al. in Biosci. Biotechnol. Biochem. There are approximately nine Major Royal Jelly Proteins and the sequences of the Major Royal Jelly Proteins 1-5 are shown below.

The term "fluorescence" as used throughout this specification in relation to honey or apalbumin or a Major Royal Jelly Protein is the wavelength that corresponds substantially to the maximum emission of light predominantly in the region of 440-560 nm when excited by light of lower wavelength.

"Royal jelly" is a honey bee secretion that is secreted from the glands in the hypopharynx of worker bees. Aside from water, protein is the major component of royal jelly.

Tissue that is "inflamed" is defined as tissue in which an immune response has occurred in response to injury or infection in the tissue, and in which the tissue has one or more symptoms of: pain, swelling, heat, sensitivity or redness.

As used herein, "anti-inflammatory capacity" is defined as the capacity to clinically reduce inflammation or the symptoms of inflammation in cellular tissue. Anti-inflammatory capacity may be determined using the phagocytosis inhibition assay (PIA) described in detail, below or the DCFDA assay described in detail below.

"Modification" of a primary amino acid sequence is understood to include "deletions" (that is, polypeptides in which one or more amino acid residues are absent), "additions" (that is, a polypeptide which has one or more additional amino acid residues as compared to the specified polypeptide), "substitutions" (that is, a polypeptide which results from the replacement of one or more amino acid residues), and "fragments" (that is, a polypeptide consisting of a primary amino acid sequence which is identical to a portion of the primary sequence of the specified polypeptide).

"Modified apalbumin" is to be understood to include any apalbumin protein or fragment thereof that has been modified by the chemical reaction of methylglyoxal on the amino acids or the chemical reaction of methylglyoxal on the side chains of the amino group that make up the protein. Methylglyoxal modifications are likely to occur on the free amino groups of the lysine, arginine and/or cysteine amino acids within the apalbumin and the terminal amino acid and such MGO modifications may occur on approximately 1-40 sites within the protein. For example, modified apalbumin1 means Apa1 modified at one or more sites on its amino acid sequences to provide a MGO modified Apa1.

Amino acid "sequence similarity" or "sequence identity" refers to the amino acid to amino acid comparison of two or more polypeptides at the appropriate place, where amino acids are identical or possess similar chemical and/or physical properties such as charge or hydrophobicity. Based on the comparison, a "percent identity" then can be determined between the compared polypeptide sequences.

BRIEF DESCRIPTION OF THE SEQUENCES

SEQ ID NO: 1—amino acid sequence of Apa1 (also known as Major Royal Jelly Protein 1) obtained from http://www.uniprot.org/uniprot/O18330.

```
              10         20         30         40         50         60
       MTRLFMLVCL GIVCQGTTGN ILRGESLNKS LPILHEWKFF DYDFGSDERR QDAILSGEYD 70         80         90        100        110        120
       YKNNYPSDID QWHDKIFVTM LRYNGVPSSL NVISKKVGDG GPLLQPYPDW SFAKYDDCSG 130        140        150        160        170        180
       IVSASKLAID KCDRLWVLDS GLVNNTQPMC SPKLLTFDLT TSQLLKQVEI PHDVAVNATT 190        200        210        220        230        240
       GKGRLSSLAV QSLDCNTNSD TMVYIADEKG EGLIVYHNSD DSFHRLTSNT FDYDPKFTKM 250        260        270        280        290        300
       TIDGESYTAQ DGISGMALSP MTNNLYYSPV ASTSLYYVNT EQFRTSDYQQ NDIHYEGVQN 310        320        330        340        350        360
       ILDTQSSAKV VSKSGVLFFG LVGDSALGCW NEHRTLERHN IRTVAQSDET LQMIASMKIK 370        380        390        400        410        420
       EALPHVPIFD RYINREYILV LSNKMQKMVN NDFNFDDVNF RIMNANVNEL ILNTRCENPD

430
       NDRTPFKISI HL
```

The Lysine (K) 22 sites and Arginine (R) 17 sites have been highlighted to identify the possible sites of glycation by MGO, whereby such glycation gives rise to a MGO-modified apalbumin.

SEQ ID NO: 2—amino acid sequence of Major Royal Jelly Protein 2 obtained from http://http://www.uniprot.org/uniprot/O77061 is shown in the Sequence Listing.

SEQ ID NO: 3—amino acid sequence of Major Royal Jelly Protein 3 obtained from http://www.uniprot.org/uniprot/Q17060-1 is shown in the Sequence Listing.

SEQ ID NO: 4—amino acid sequence of Major Royal Jelly Protein 4 obtained from http://www.uniprot.org/uniprot/Q17060-1 is shown in the Sequence Listing.

SEQ ID NO: 5—amino acid sequence of Major Royal Jelly Protein 5 obtained from http://www.uniprot.org/uniprot/O97432 is shown in the Sequence Listing.

MGO-Modified Apalbumin 1

Apalbumin 1, also known as Apa1 or "Major Royal Jelly Protein 1" (MRJP1) is a protein found in varying concentrations in various bee products. Apa1 is a 48.9 kilodalton (kDa) protein secreted by bees, and it is found in honey, royal jelly, and other bee products. All varieties of honey tested have been shown to contain Apa1 (J. Simuth et. al, 2004). Apa1 is estimated to constitute 48% of the proteins in royal jelly (B. Lerrer et. al, 2007).

Methylglyoxal or MGO is a highly chemically reactive compound with the formula $C_3H_4O_2$. MGO is formed by multiple metabolic pathways in living organisms. Certain preparations of manuka honey, which are referred to as "active" manuka honey, contain much higher concentrations of MGO than other varieties of honey. Active manuka honey has been determined to contain MGO concentrations up to 1000-fold greater than the MGO concentration in other varieties of honey (E. Mavric et al, 2008).

MGO can participate in a variety of chemical reactions in living organisms, including the formation process of "Advanced Glycation Endproducts" (AGEs). Glycation is the reaction of a sugar with a protein or a lipid without the involvement of an enzyme as a catalyst for the reaction. MGO can glycate proteins by reacting with the free amino groups of the amino acids arginine, lysine and/or cysteine and the terminal amino group, and thereby can chemically modify proteins that contain arginine and/or lysine. As can be seen from SEQ ID NO: 1 Apa1 contains a total of approximately 39 arginine and lysine residues that may be chemically modified by MGO.

MGO-modified Apa1 can be derived by isolation of the molecule from active manuka honey. MGO-modified Apa1 can be isolated from honey and/or enriched from honey by biochemical techniques. These techniques include but are not limited to filtration, centrifugation, and chromatography, such as ion-exchange, affinity, hydrophobic interaction, size exclusion, and reverse-phase chromatography. MGO-modified Apa1 can also be purified from various sources or chemically synthesized by addition of MGO to royal jelly.

MGO-modified Apa1 may also be derived by obtaining a gene coding for the amino acid sequence SEQ ID NO: 1, cloning the gene into an appropriate vector, transforming a cell line with the vector, causing the polypeptide to be expressed, purifying the polypeptide, mixing the polypeptide with MGO to allow for chemical reaction between MGO and the polypeptide, and purifying the MGO-modified polypeptide.

Expression systems may contain control sequences, such as promoters, enhancers, and termination controls such as are known in the art for a variety of hosts (See e.g. Sambrook et al., *Molecular Cloning: A Laboratory Manual*, Second Ed., Cold Spring Harbor Press (1989) which is incorporated herein in its entirety). The expression systems may also contain signal peptide and proprotein sequences that facilitate expression of the gene and/or folding of the protein.

MGO-modified forms of amino acid variants of Apa1 (SEQ ID NO: 1) may also exhibit anti-inflammatory capacity. As would be understood by one of ordinary skill in the art, minor modification of the primary amino acid sequence of SEQ ID NO: 1 may result in a polypeptide which has substantially equivalent or enhanced anti-inflammatory activity as compared to SEQ ID NO: 1. When Apa1 modification includes one or more substitutions, preferred substitutions are those that are conservative, i.e., wherein the residue is replaced by another of the same general type. In making modifications to the Apa1 protein, the hydropathic index of amino acids may be considered (See, e.g., Kyte. et al., J. Mol. Biol. 157, 105-132 (1982), herein incorporated by reference in its entirety). It is known in the art that certain amino acids may be substituted by other amino acids having a similar hydropathic index or score and still result in a polypeptide having similar biological activity.

Preferably, the MGO-modified Apa1 variant exhibits at least about 75% sequence identity to the non-variant Apa1 sequence, preferably at least about 80% identity, more preferably at least about 85%, 90%, 91%, 92%, 93%, 94%, 95%, 96%, 97%, 98%, 99% or 100% sequence identity to any wild type or reference sequence described herein. Even more preferably, the MGO-modified Apa1 variant exhibits anti-inflammatory capacity substantially comparable to that of non-variant MGO-modified Apa1.

The formation of MGO-modified Apa1 in honey can be stimulated by (i) prolonged storage at ambient temperature, or (ii) incubation of honey at elevated temperatures (30-40 Celsius), thereby increasing the anti-inflammatory capacity of a sample of honey. Addition of MGO or an MGO precursor, such as dihydroxyacetone (DHA) to a sample of honey, along with sufficient time and/or heating to convert the MGO precursor to MGO, may also stimulate the formation of MGO-modified Apa1 in that sample of honey, and may also increase the anti-inflammatory capacity of the sample of honey, by the generation of MGO-modified Apa1 in the honey sample.

Apa1 with enhanced anti-inflammatory properties can also be formed outside of honey. Completely or partially purified Apa1 has been found to be treatable with MGO, in order to yield MGO-modified Apa1. The MGO-modified Apa1 exhibits enhanced anti-inflammatory properties when compared to the non-modified Apa1.

MGO-modified Apa1 and variants thereof may be included in therapeutically-effective amounts in pharmaceutical compositions. The pharmaceutical compositions of the present disclosure may be specially formulated for administration in solid or liquid form, including those adapted for the following: (1) oral administration, for example, drenches (aqueous or non aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained release formulation; (3) topical application, for example, as a cream, ointment, or a controlled release patch or spray applied to the skin; (4) intravaginally or intrarectally, for example, as a pessary, cream or foam; (5) sublingually; (6) ocularly; (7) transdermally; (8) pulmonarily, or (9) nasally. When the compounds of the present invention are administered as pharmaceuticals, to humans and animals, they can be given per se or as a pharmaceutical composition containing, for example, about 0.1 to 99%, or about 1 to 50%, or about 10 to 40%, or about 10 to 30, or about 10 to 20%, or about 10 to 15% of active ingredient in combination with a pharmaceutically acceptable carrier.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the pharmaceutical compositions described herein. These compositions may also contain adjuvants such as preservatives, wetting agents, emulsifying agents and dispersing agents. Prevention of the action of microorganisms upon the compounds of the present invention may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Example 1

Isolation of MGO-Modified Apalbumin Protein from Manuka Honey

A sample of manuka honey obtained from the Honey Research Unit, University of Waikato, NZ and had a non-peroxide antibacterial activity equivalent to 12% w/v phenol (Allen, Molan et al. 1991), was fractionated as follows:

1.1 Elimination of the Low Molecular Weight Components of Honey

Twenty-five grams of manuka honey were suspended in 25 ml of distilled water and dialyzed (Cellu Sep T1 tubing, Membrane Filtration Products, Inc., Seguin, Tex.; EEUU, molecular mass cut off 3500 Da) against 1 liter of tap water for 48 h at 4° C. with four changes of the 1 liter of water during this time. The dialysis retentate was lyophilized and then stored at −20° C. until analysis. The lyophilized samples were reconstituted to 2 ml with 0.3 mol/l ammonium acetate buffer.

1.2 Chromatographic Separation on Sephadex G-50

Figure 3:
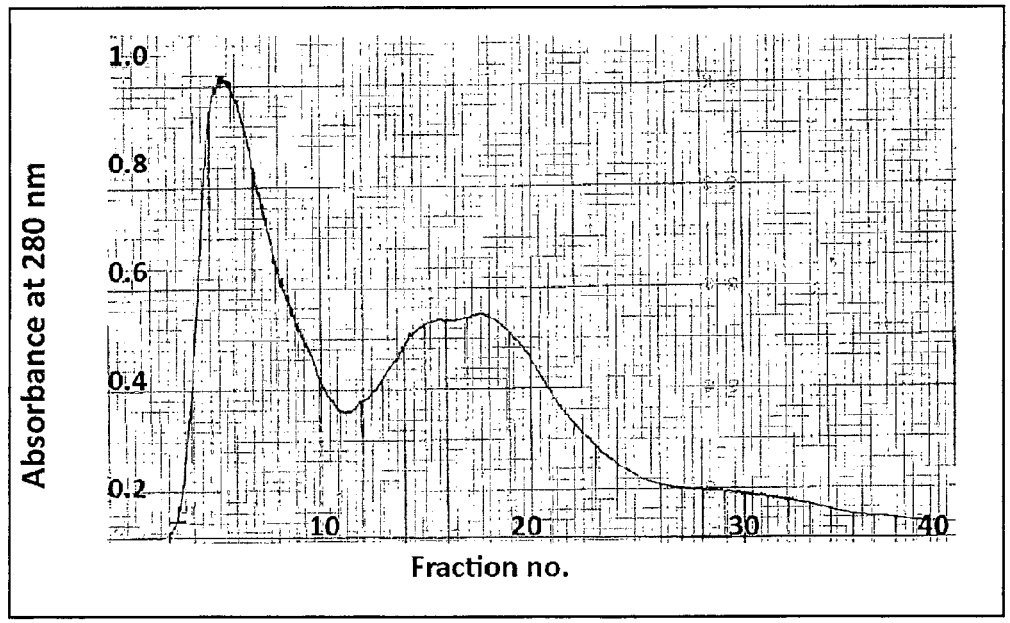
FIG. 3 shows the elution from chromatography of the dialysis retentate of Manuka honey on a 180 ml G-50 Sephadex column. The fraction size was 1 ml.
Figure 4:
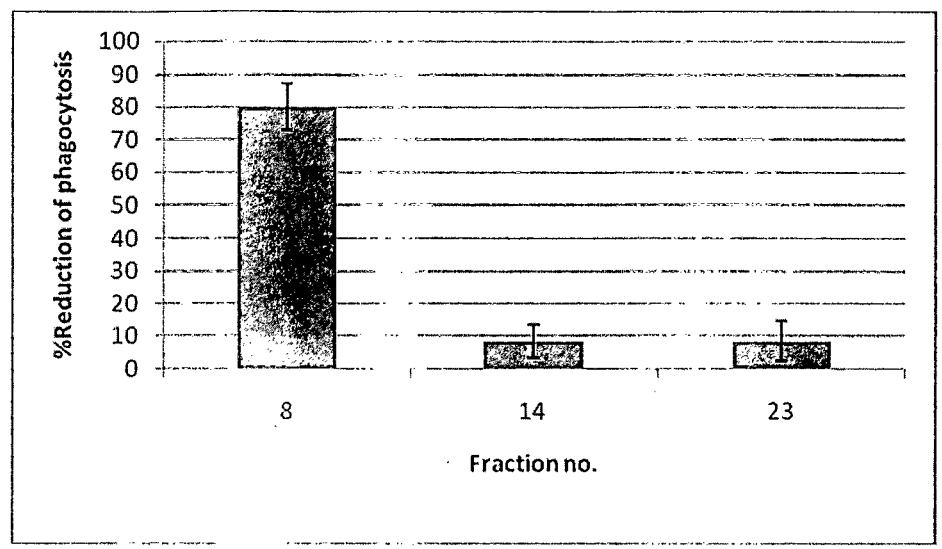
FIG. 4 shows the phagocytosis-inhibiting activity of Fractions 8, 14 and 23 obtained from G-50 Sephadex chromatography shown in FIG. 3. Results show % reduction of phagocytosis compared with that by the non-treated control. Error bars show ±1 SD of the mean from at least three assays. Fraction 23 was included as a control as it contained little/no protein.
Figure 5:
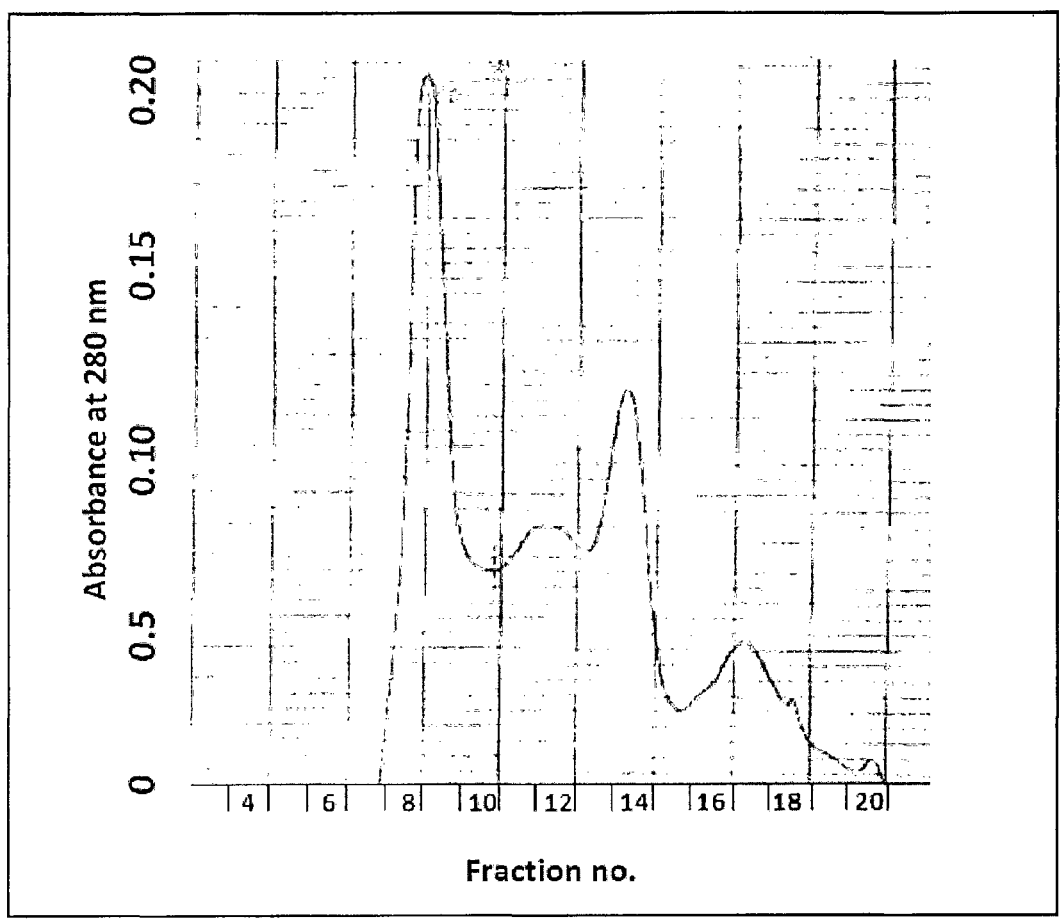
FIG. 5 shows the elution profile from chromatography on a 25 ml Superose 12 FPLC column of Fractions 4-10 from chromatography on Sephadex G-50. The fraction size was 1 ml.

The reconstituted retentate from dialysis (2 ml) was then loaded onto a Sephadex G-50 column (180 ml) and the material was eluted in 1 ml fractions (flow rate 0.5 ml/minute monitored at 280 nm). The fractions obtained from the 2 peaks shown in FIG. 3 were lyophilized and reconstituted to 100 µl with purified water for preliminary assessment in the phagocytosis assay. This assay indicated that the inhibitory activity was in the peak that was eluted first. Further chromatographic separation was undertaken to generate a larger amount of protein. The chromatography on the Sephadex G-50 column was repeated three times and the fractions in the first peak on the elution trace from each run were pooled together, rotary evaporated to 200 µl and then separated on a Superose 12 column.

1.3 Fast Protein Liquid Chromatography (FPLC) Separation of Protein on Superose 12

To further fractionate the first peak on the Sephadex G-50 elution trace, a 100 µl amount of the reconstituted sample was injected on a Superose 12 FPLC column (25 ml) and eluted as 1 ml fractions with phosphate-buffered saline (pH 7.11), flow rate 0.5 ml/minute, 0.5 cm/ml, monitored at 280 nm. These fractions were frozen at −20° C. until further use. Two clearly separated major peaks (Fractions 8 and 14) obtained were assayed for inhibitory activity in the phagocytosis assay. These fractions were run on a 10% SDS-PAGE gel and processed for MALDI-TOF mass spectrometry identification.

1.4 Reverse Phase of Active Fractions

The fraction from chromatography on Superose 12 found to have phagocytosis-inhibiting activity (Fraction 8) was chromatographed on a reverse phase column to further purify proteins for MALDI mass spectrometry identification. Chromatography was performed using a column on a FPLC system (Pharmacia-LKB, Uppsala, Sweden). A 500 µl amount of the Fraction 8 sample was injected on the column and eluted with a mobile phase in a gradient from 100% water to 100% of acetonitrile at a flow rate of 1 ml/minute monitored at 260 nm. The fractions comprising the two major peaks obtained (Fractions 23 and 26) were rotary evaporated to 50 µl. The fractions (5 µl) were loaded onto 10% SDS mini gels to visualise and processed for MALDI-TOF mass spectrometry as described below.

Example 2

Phagocytosis Inhibition Assay (PIA) Using THP-1 Cells

Phagocytosis is a cellular response or process of engulfing solid particles and in the immune system it is a major mechanism used to remove pathogens and cell debris. Bacteria, dead tissue cells, and small mineral particles are all examples of objects that may be phagocytosed or engulfed by a cell. Phagocytosis occurs at the beginning of the inflammatory response of leukocytes to a trigger of inflammation. Reactive oxygen species and cytokines that are produced by cells when phagocytosis is activated in them recruit and activate more phagocytes as part of a cascade of cellular events which are the inflammatory response that all begins with phagocytosis. Thus any inhibitor of phagocytosis effectively stops the inflammatory response right at the start of the cascade.

The phagocytosis-inhibiting activity of a range of types of New Zealand honey was measured. Manuka honey was found overall to have a much higher activity than other types, as shown in the following Table 1, which shows the effect of different types of honey (0.5%) on phagocytosis of latex particles in LPS-activated THP-1 cells. The assay was performed 4 h after latex particle addition. Manuka and artificial honey concentrations were achieved by dilution of the honey with sterile RPMI 1640 complete medium. Manuka honey was obtained from the Honey Research Unit, University of Waikato, NZ and had a non-peroxide antibacterial activity equivalent to 12% w/v phenol (Allen, Molan et al. 1991). Honey was diluted by weighing 1.37 g (density of honey per ml) and diluting this with 19 ml of MilliQ water (5% V/V concentration) immediately prior to use in sterile RPMI 1640 and filtered (50 µm, 8 µm and 3 µm, Minisart Sartorius filters, Millipore corporation) to remove pollen, bee tissues etc. Undiluted honey was kept at 4° C. in dark coloured containers to prevent enzyme denaturisation and degradation. Artificial honey was used to provide a control for the osmotic effect of the natural sugars found in honey. The composition of this was as published (White 1975).

It is well known that some types of honey produced in New Zealand may have had some manuka nectar also included in them whilst being produced by the bees because manuka grows extensively throughout New Zealand and is a favoured source of nectar for bees.

TABLE 1

| Honey type | Percent reduction in phagocytosis |
| --- | --- |
| Pasture honey | 13% ± 4% |
| Clover honey | 6% ± 4% |
| Kanuka honey | 15% ± 3% |
| Manuka honey | 67% ± 10% |
| Artificial honey | 0% |

THP-1 is a well-characterized human monocytic leukemic cell line. The cells resemble monocytes with respect to several criteria and can be differentiated into macrophage-like cells by treatment with PMA, LPS or Vit D (Auwerx J., 1991). Once activated the macrophage can be used to study phagocytosis by incubating the macrophages with latex beads or similar and recording the phagocytic uptake by observing the cells under a microscope. By using fluorescent latex beads the beads are visible inside the cell after phagocytosis. Substances that inhibit phagocytosis can be studied by comparing the amount of phagocytosis when the substance is added with the amount of phagocytosis without the substance added.

Changes in cell morphology, phagocytosis, rate of cell division, and selected surface markers were evaluated in cultures of THP-1 cells exposed to honey after activation with LPS, PMA and Vit-D. LPS was selected for further research as the activation rate is shorter enabling the assay to be completed within 30 hours. LPS-activated cells become macrophages in 24 hours whereas with PMA and Vit D it takes at least 72 hrs. The criteria for differentiation of THP-1 cells were cell adherence, changes in cell morphology, and changes in the cell surface marker expression profile of human cartilage group protein-39 (HCgp-39) and carboxypeptidase M (CPM) that are associated with the macrophage phenotype, determined by qRT-PCR of mRNA from LPS treated and untreated cells.

THP-1 cells were maintained at 37° C., 5% $CO_2$, and 95% relative humidity (RH) in endotoxin-free RPMI 1640 medium containing 10% fetal calf serum and 25 mM HEPES with antibiotics. Cells were sub-cultured every 3 days to maintain cell counts around $10^6$/ml and viability was assessed on a haemocytometer by means of trypan blue exclusion before treatments. Passage number was always between 40 and 55.

A 100 ug/ml stock solution of LPS was prepared by dissolving 1 mg LPS in sterile RPMI 1640 (Invitrogen). The stock solution was stored frozen at −20° C. Immediately prior to use, the LPS stock solution was thawed and added to freshly sub-cultured cells to a final concentration of 500 ng/ml with $10^6$/ml THP-1 cells with a viability 95% or higher. Cells were plated out at 1 ml per well in a 24 well plate (Cellstar, Greiner bio-one) and the plate sealed with tape to avoid evaporation. Plates were incubated for 24 hours 37° C., 5% $CO_2$, and 95% relative humidity (RH) to allow activation.

Prior to the phagocytosis assay, each well was checked on an inverted microscope to observe morphology changes which indicate a successful transformation. Control THP-1 cells (no LPS) maintained a round shape and did not clump or adhere to the culture plate surface whereas activated THP-1 cells treated with LPS aggregated, became flat and amoeboid with obvious pseudopodia, and adhered to the culture plate surface.

Monolayers of LPS-activated THP-1 cells were washed twice with sterile RPMI medium, removing the suspended cells, and then incubated with either one of three treatments; no honey, artificial honey (0.25%) or honey (0.25%) for 30 minutes in 500 µl RPMI. Sterile 1.0 µm coated polystyrene latex beads (Sigma L5405-1 ml) approx 25 beads per cell were added to the monolayers and plates incubated 37° C., 5% $CO_2$, and 95% RH. Each treatment group had at least three replicates per experiment and repeated at least twice on separate days.

After four hours of incubation suspended cells were removed and phagocytosis halted by washing the monolayer with ice-cold sterile phosphate-buffered saline. Adherent cells were loosened from the plate by gentle pipetting of 100 µl PBS up and down on the well. At least 200 cells from each sample were counted on a haemocytometer using an Axostar plus Zeiss fluorescent microscope phase II with a 40× lens. Cells that contained at least three beads were considered positive for phagocytosis. Non-activated THP-1 cells (monocytes) had less than 5% phagocytosis rate observed in preliminary assays. Viability was checked after the assay using the trypan blue exclusion method to ensure treatments or honeys had not induced apoptosis.

The ability of THP-1 cells to phagocytise latex beads is quantified with a percentage of honey treatment/no honey control. First the activation rate was obtained by dividing the number of phagocytic cells by the number of cells counted on a haemocytometer. Acceptable activation rates for four hours of incubation was 70% or greater. The honey treatments were also counted in this manner and then a percentage reduction of phagocytosis was calculated according to the following formula.

% reduction of phagocytosis=(honey treatment phagocytosis rate/control)×100−100

An exemplary calculation follows:
Control, 75% (75% of the cells phagocytosed at least 3 beads)
Honey treatment 1, 25% (25% of the cells phagocytosed at least 3 beads)
Honey treatment 1, phagocytosis-inhibiting activity=(25/75)×100−100=66.7%

This result indicates that honey treatment 1 had a 66.7% inhibitory effect on the phagocytic uptake of latex beads.

For screening lots of samples this assay can be modified to work on a 96 well plate using a modified protocol set out by (Wan, Park et al. 1993). This assay has been modified to use THP-1 and its growing conditions/media and the same latex beads. Wells are washed in PBS after incubation with honey to remove suspended cells and free latex beads before measurement on either a plate reader or the LAS-1000. Both methods have been compared and give fairly similar results.

Example 3

Measurement of Fluorescence Intensity

The fluorescent intensity of honey is measured on a Fujifilm LAS-100 equipped with an intelligent darkbox II (Alphatech). Data is analysed using the provided software, Image Reader LAS-1000 plus lite version 1.5 and Image Gauge 4.0.

Honey is brought to room temperature and diluted to 10% v/v (1 ml honey=1.37 gm) in double-distilled $H_2O$. 5 ml of dilute honey is then filtered through a 0.2 µm Minisart sterile single use syringe filter (Sartoris). 100 µl of dilute honey is pipetted into 5 wells of a 96 well black plate (nunc CAT 137101). A standard honey with known fluorescence is also plated along with a water blanks and empty wells for background readings.

The plate is placed inside the darkbox (level 4) and focused using the Image reader LAS 1000 plus programme. A pre-exposure is taken to gauge the required exposure time which is approximately 30 seconds. Once the image is taken results are obtained using the provided Image Gauge 4.0. Briefly, the fluorescence is measured across the well in arbitrary units (AU) and the background intensity is subtracted to give a reading ranging from 40000 AU to 260000 AU. Samples are averaged to obtain a final reading with typical standard deviation+/−1500 AU. In some cases the fluorescence intensity is too high and exposure time is reduced to avoid over exposure. The standard honey AU is used to derive the correct AU for these honeys (though this is rarely done as only a few honeys have been this fluorescent).

1% of the concentration they would have been in honey. A 200 µl assay sample size was used due to the smaller amounts of protein available from the fractioning of honey. Fraction 8 and 14 obtained as described above were assayed for phagocytosis-inhibitory activity. Fraction 8 had strong phagocytosis inhibiting activity and fraction 14 had very little activity. Both fractions were identified with significant hits by MALDI-TOF mass spectrometry as described below. The fraction with the majority of the anti-inflammatory activity (Fraction 8) was modified Apalbumin 1 (MRJP-1). Fraction 14 returned two hits, one being significant which was Apalbumin 3 (MRJP-3). The non-significant hit was Apalbumin 1 (MRJP-1), most likely being unmodified by MGO.

Example 4

Electrophoresis on SDS Mini Gels

Proteins obtained by fractionation of honey were run on SDS-PAGE gels to visualise and give a molecular weight estimate. Resolving gels with 10% and 12% acrylamide were used for separating a different range of proteins. The 10% gel is best for separating 14-205 kD proteins and 12% gel for 14-66 kD proteins. The gels were made in an OWL Separation System gel caster (BioLab Scientific LTD) using assembled clean glass plates. The resolution gel was poured first, using a syringe, and left to set covered with a layer of butanol to ensure an even gel surface. When the gel was set the butanol was removed and the stacking gel was poured and a gel comb inserted to make wells for sample loading. The composition of the gels was:

10% Resolution Gel
  6.8 ml 37% Acrylamide
  2 ml 1M Tris pH 9.0
  5.9 ml water
  150 µl 10% Sodium Dodecyl Sulfate (SDS)
  15 µl N,N,N',N' tetramethylenediamine (TEMED)
  150 µl 10% ammonium persulfate (APS)
12% Resolution Gel
  8.2 ml 37% Acrylamide
  2 ml 1M Tris pH 9.0
  4.5 ml water
  150 µl 10% SDS
  15 µl TEMED
  150 µl 10% APS
5% Stacking Gel
  0.66 ml 37% Acrylamide
  1.25 ml 0.5M Tris pH 6.8
  3.0 ml water
  50 µl 10% SDS
  5 µl TEMED
  50 µl 10% APS When the stacking gel was set, the gel was inserted into the electrophoresis chamber and running buffer (3.0 g Tris, 14.4 g Glycine, 1 g SDS, in 1 l MilliQ water) added in the top and bottom chamber. The comb was removed and the sample wells washed with electrophoresis buffer. The gel was then run for 10 minutes at 10 mA to remove any un-polymerised acrylamide. Samples to be loaded on the gel were mixed 1:1 with 2× Tricine Sample Buffer (0.1 mol/l Tris pH 6.8, 24% (w/v) glycerol, 8% (w/v) SDS, 0.2 mol/l dithiothreitol, 0.02% (w/v) Coomassie Blue G-250) and heated at 99° C. for 5 minutes, then left to cool. Samples were centrifuged (2000×g for 20 seconds) to pellet any sediment and 10 µl of sample loaded per lane. A BIORAD Precision Plus Dual Colour protein standard ladder (Cat. No. #161-0374) was run alongside the samples to provide an estimated protein size for the samples. The standard contained proteins sized 10-250 kDa: 6 µl was loaded at each end of the gel. The gel was run at 10 mA until samples had migrated through the stacking gel into the resolution gel. The current was then increased to 20 mA. When the dye in the sample had run off the edge of the gel, the current was switched off and the gel removed and stained. Two methods were used to visualize bands. Silver staining was used to identify fainter bands as it is more sensitive. A fast blue method was used prior to MALDI-TOF mass spectrometry work as the stain is more readily removed than silver. Fast blue is a stain using Coomassie Brilliant Blue which binds with less affinity to glycoproteins making it ideal for honey which has a large proportion of glycoproteins. This allows for better stain removal prior to protein MALDI mass spectrometry work as remaining stains can interfere with quantification (Deutscher 1990). All reagents were made fresh 5 minutes before staining took place and kept at 4° C. until required. The gel was first fixed for 30 minutes in 50% ethanol/12% acetic acid, then soaked in 30% ethanol for 15 minutes. Then 100 ml of 0.02% sodium thiosulfate was added and left for 1-2 minutes. The gel was soaked in 100 nil 0.1% silver nitrate+100 µl formaldehyde for 10 minutes. It was then washed in water for 10 seconds and 100 ml developer (3 g sodium carbonate, 100 µl formaldehyde, 40 µl 1% sodium thiosulfate in 100 ml MilliQ water) added. Development was stopped with 10% acetic acid after the bands became visible. Developed gels were stored in MilliQ water until required. Fast Blue was obtained from Fisher Biotec (Cat. No. #FS-100). Fast Blue was diluted (8 ml of Fast Stain concentrate, 32 ml MilliQ water, 10 ml 45% methanol with 10% acetic acid) before use. Gels were first washed in 40% methanol with 10% acetic acid for 10-20 minutes followed by a rinse in MilliQ water. Then 100 ml of diluted Fast Blue was added and the gel was gently swirled in the solution for 20 minutes. Gels were de-stained with 10% acetic acid for 10 minutes, then stored in MilliQ water until required.

The molecular weight for Fraction 8 (Apa1/MRJP-1) estimated from the SDS gels is 60 kDa which is 10 kDa larger than would be expected as the Swiss-prot returned a protein size of only 48.9 kDa. The size disparity could be explained by glycosylation and/or cross-linking. Three predicted N-linked glycosylation sites have been reported on MRJP-1 (Srisuparbh, Klinbunga et al. 2003). Glycation of these sites would increase the molecular weight. As Fraction 8 was in the void volume, (meaning macromolecules that are sufficiently large to be excluded from the column beads elute first from the column (the void volume of the Superose 12 column is 11 ml), this may indicate that the Apa1/MRJP-1 is highly glycosylated and/or cross-linked, as at 48.9 kDa (the molecular weight of Apa1/MRJP-1) the monomer protein should easily enter the column.

Example 5

MALDI-TOF Mass Spectrometry Identification of Active Honey Proteins

The MALDI-TOF work described below was completed at the Waikato Mass Spectrometry Facility, University of Waikato.

5.1 Preparation of Proteins

A clean scalpel was used to excise the bands which were then de-stained with 30% ethanol to remove the Fast Blue dye by incubating at 60° C. for 15 minutes or until the gel pieces appeared colour-less. The bands were washed twice in 30% ethanol and then shrunk with 100% acetylnitrile for 10 minutes. Acetylnitrile was removed by aspiration and the gel piece was dried by vacuum in a Speed Vac to remove residual moisture for 30 minutes. The protein in the gel pieces was cleaved into peptides for analysis by MALDI-TOF mass spectrometry by digesting the protein in the gel piece with trypsin. The method used was adapted from details given by Jo McKenzie, University of Waikato. To each gel piece 10 µl of 25 mmol/l ammonium bicarbonate was added, followed by 10 µl of sequencing grade trypsin solution (49 µl 25 mmol/l ammonium bicarbonate in 10% acetylnitrile, 1 µl sequencing trypsin (1 mg/ml Promega Cat. No. #V5111). Tubes were then left overnight at 37° C. To each tube 14 µl 50% acetylnitrile with 0.3% trifluoroacetic acid was added and the tubes vortexed and sonicated for 10 minutes. The gel piece was discarded and the solutions were refrigerated until use.

5.2. Preparation of Matrix

The method used was obtained from Waikato Mass Spectrometry Facility, University of Waikato. 5 mg α-Cyano-4-hydroxycinnamic acid (CHCA) was added to 500 µl 65% acetylnitrile with 1% trifluoroacetic. The solution was vortexed for 2 minutes, sonicated for 10 minutes, vortexed again for 2 minutes then centrifuged at 12,000 rpm for 5 minutes. The prepared protein digest solutions and matrix were combined (2:1) and 1 µl was spotted onto the MALDI Anchor chip target plate. The spots were allowed to air dry and then washed by pipetting 5 µl of 1% trifluoroacetic onto and off the dried matrix spot and allowed to dry.

5.3 Autoflex Operating Procedure

The external calibration was conducted with the Bruker Daltonics Peptide standard 206195 prior to analysis. A monoisotopic peptide calibration was used with a zooming of ±0.1%. Once a good, clean spectrum has been collected the mass spectrometer is automatically recalibrated. The fit result is accepted if the error is no more than ±10 ppm. Internal calibration can be conducted if products resulting from the autolysis of the trypsin are present. These products yield peaks at 842 and 2 211. The peaks are assigned as internal calibrants in the flex analysis program. A Bruker Autoflex II TOF/TOF mass spectrometer was used to analyze peptide digests. An average of 30 shots per sample was taken to build the peptide mass fingerprint spectra. The mass range selector was set at low range and the detector gain voltage offset was set at 1 400 v. The detection settings were set in the range of 480-3 540 Da. The instrument was manually operated using flex control software. Suitable spectra were saved and exported into flex analysis.

5.4 Analysing MALDI Spectra

Using the Biotools software the spectrum collected can be searched against a variety of protein databases. The databases of preferred use are SWIS Prot and NCBInr. The parameters for the searching of Eukaryota proteins in SWIS Prot are a peptide tolerance off 200 ppm and 1 missed cleavage. A protein score greater than 64 is significant for Swis Prot. The parameters for searching of Eukaryota proteins, in NCBInr are 1 missed cleavage and a peptide tolerance of ±200 ppm. The protein Score required for a significant hit in NCBInr is 78. These parameters where correct, at least, up until May 2009. Molecular masses can be measured to within an accuracy of 0.01% of the total molecular mass of the molecule/peptide. This is sufficient to allow minor mass changes to be detected, e.g. the substitution of one amino acid for another or a post-translational modification.

The main function of the mass analyser is to separate, or resolve, the ions formed in the ionisation source of the mass spectrometer according to their mass-to-charge ratios. The peptides produced by the tryptic digest are separated by ionisation due to their mass and this mass can be calculated. The detector monitors the ion current, amplifies it and the signal is then transmitted to the data system where it is recorded in the form of a mass spectrum. The mass to charge values of the ions are plotted against their intensities to show the number of components in the sample, the molecular mass of each component, and the relative abundance of the various components in the sample. When using MALDI-TOF to identify a protein, the ions generated must form a clear mass spectrum with intense peaks, indicating that only one protein (in large quantities at least) is present in the band cut from the SDS electrophoresis gel. When more than one protein is present in the sample there is typically no clear peaks correlating to large amounts of the same peptide.

5.5 MALDI-TOF Mass Spectrometry Identification of Active Proteins

Figure 7:
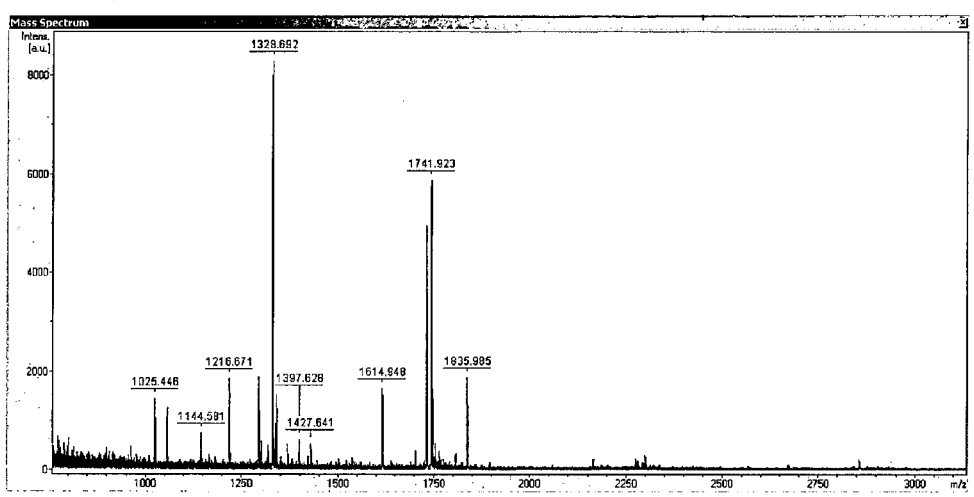
FIG. 7 shows the mass spectrum of peptides obtained by tryptic digest of Fraction 14 isolated with a Superose 12 chromatography column.

The proteins recovered from the excised bands in the gels from SDS electrophoresis as described above, Fractions 8 and 14 from the Superose 12 chromatographic separation, were subjected to a tryptic digest for MALDI-TOF mass spectrometry analysis for identification. The Autoflex operating procedure described above was used to obtain a peptide mass fingerprint spectrum of Fraction 14 isolated from the Superose 12 chromatography column. The mass spectrum generated by MALDI-TOF mass spectrometry as shown in FIG. 7 provided a molecular weight for each peptide and this was entered into the SWIS Prot library and searched for matches. Two hits/matches of the molecular weight of the tryptic peptides to the SWIS Prot library were obtained. The most significant hit/match was for the protein Apalbumin 3 (MRJP-3). The second hit Apalbumin 1 (MRJP-1), is not a significant match in itself, but because the mass spectrum peaks which correspond to this match are different from the ones which contribute to the match for MRJP-3, it is very likely to be present in the sample.

Figure 6:
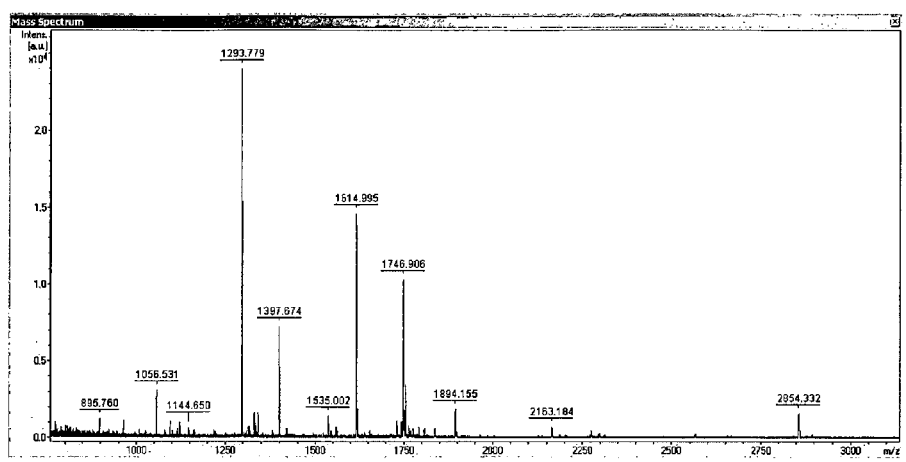
FIG. 6 shows the mass spectrum of peptides obtained by tryptic digest of Fraction 8 isolated with a Superose 12 chromatography column.

The same procedure was also carried out for Fraction 8 isolated from the Superose 12 chromatography column. The MALDI mass spectrum of the peptides from Fraction 8 as shown in FIG. 6 provided one significant hit for the mass spectrum, a match for MRJP-1.

Example 6

Incubation of Honeys in the Presence of MGO

Both Manuka and non-Manuka honeys were incubated. Manuka honey was selected for incubation based on its initial high MGO levels and low fluorescence. Non-Manuka honey was selected based on its low fluorescence and lack of MGO. Honey was incubated for three months, during which time fluorescence readings were tracked. Each honey incubated also had a sample frozen to maintain the original qualities. The incubated honey and the frozen honey were assayed for inhibition of phagocytosis and were subjected to SDS electrophoresis on a mini-gel to determine any protein size modifications due to the incubation. A Manuka honey with high fluorescence and Manuka honey with low fluorescence was also subjected to SDS electrophoresis for comparison to the incubated and non-incubated honey. Whole Clover and Pasture honeys were incubated with MGO or without MGO for three months at 37° C. to determine if the presence of MGO would generate fluorescence over time in the non-fluorescent honey and increase the phagocytosis-inhibiting activity. The honey had been assayed previously for phagocytosis-inhibiting activity and had low activity. The honey was electrophoresed on a SDS mini-gel to determine any protein size modifications due to the incubation. The MGO treated honey was assayed in the phagocytosis assay to determine what effect the incubation had on the phagocytosis-inhibiting activity. Methylglyoxal (40%) was purchased from Sigma-Aldrich (Cat. No. #M0252) and used at final concentrations correlating to a non-peroxide antibacterial activity of 15 (approximately 400 μg/gm honey or 1 ml of 40% MGO per kg honey).

6.1 Honey Incubation

Whole Manuka honey (20 g of MSB20, NPA 20+), Pasture honey (20 g) and Clover honey (20 g) were incubated for three months at 37° C. Clover honey, (20 g) treated with 400 μg/g MGO mixed into it, was also incubated for three months at 37° C. Control samples of all the honeys (20 g) were frozen for the duration. The fluorescence of honey immediately after adding the MGO was measured, and at the concentrations added to honey, the fluorescence was found to not increase due to the added MGO. After six weeks and three months incubation of the honey, the fluorescence was measured.

6.2 SDS Gel Electrophoresis of Incubated Honey

Honey samples described above were run on a 12% SDS mini-gel (prepared and run as described above) Also included for comparison was Manuka honey with high fluorescence and Manuka honey with low fluorescence. Honey was diluted to 10%. Samples to be loaded on the gel were mixed 1:1 with 2× Tricine Sample Buffer and heated at 99° C. for 5 minutes, then left to cool prior to loading. Prior to staining, gels were imaged on a UV gel illuminator to observe the fluorescence of the protein band (this fluorescence was not visible after staining). SDS minigels were silver-stained.

Table 2 below shows the fluorescence measurements for selected honeys before, during and after incubation for three months at 37° C. with natural MGO levels (Manuka) or 400 mg/kg MGO added (Pasture and Clover). In the controls which were Manuka honey (with a high natural MGO content) kept for three months at 4° C., and Pasture and Clover honey with 400 mg/kg MGO, or honey with no added MGO (Pasture and Clover), kept for three months at 4° C., there was no increase in fluorescence (results not shown).

TABLE 2

Table 2. Fluorescence measurements (in Arbitrary Units × 10$^3$) before incubation, after 6 weeks incubation, and after 3 months incubation at 37° C., with the level of natural or added MGO shown for honey . . . Manuka honey had natural MGO levels whereas Pasture and Clover had MGO added.

| Honey | MGO mg/kg | Fluorescence before incubation | Fluorescence after 6 weeks incubation | Fluorescence after 3 months incubation |
|---|---|---|---|---|
| Manuka | 576 | 88 | 149 | 170 |
| Pasture | 10 | 35 | 47 | 57 |
| Pasture | 410 | 35 | 64 | 89 |
| Clover | 0 | 41 | 52 | 60 |
| Clover | 400 | 41 | 66 | 82 |

6.3 SDS Electrophoresis Gel Images of Incubated Honeys

Figure 9:
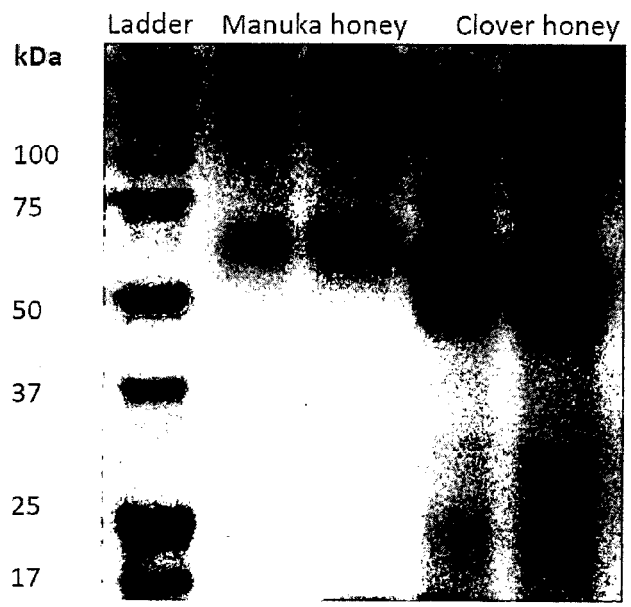
FIG. 9 shows the Silver-stained gel from SDS electrophoresis of untreated Manuka honey and Clover honey before incubation (in duplicate).
Figure 10:
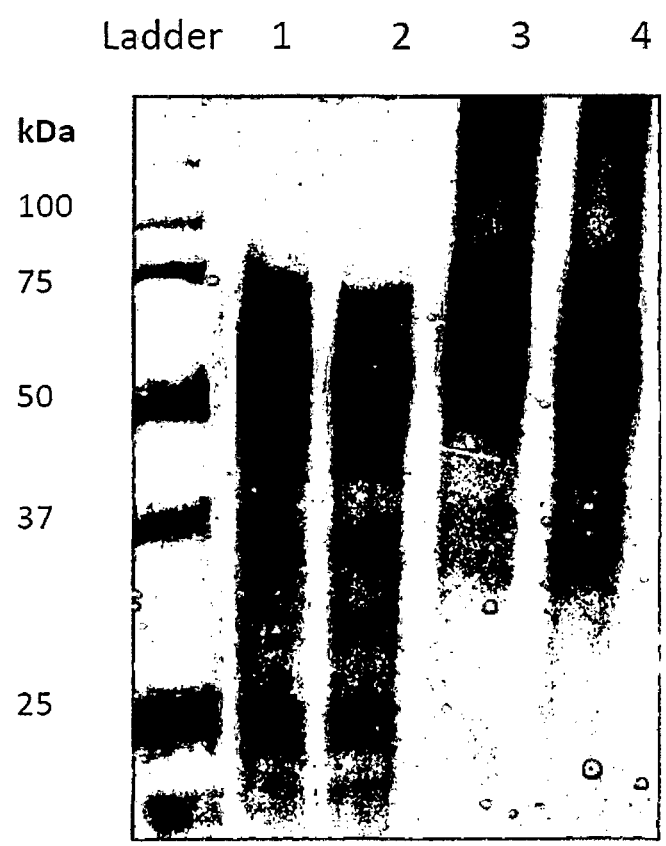
FIG. 10 shows the silver-stained gel from SDS electrophoresis of Pasture honey after 3 months incubation (Lane 1) and before incubation (Lane 2) and Manuka honey after 3 months incubation (Lane 3) and before incubation (Lane 4).

The results of electrophoresis of honeys incubated with MGO are shown in FIGS. 9 and 10. FIG. 9 shows the size difference of the major protein (60-65 kDa) between Clover honey and Manuka honey. FIG. 10 shows that incubating honey with MGO increased the size of the major protein (by about 5-10 kDa) in both honey types.

As described in detail above, activity-led fractionation was used to isolate the component(s) of the sample of manuka honey. It was found by the inventors, that the isolated component of manuka honey having phagocytosis-inhibiting activity was fluorescent. At each stage of separating the honey into fractions each fraction was tested to measure how much phagocytosis-inhibiting activity was present in it by measuring the fluorescence of the component at about 490 nm. As can be seen from FIG. 1a the emission wavelength is between 450-550 nm. It was found after dialysing manuka honey that the activity was in the dialysis retentate which was the fraction containing components of molecular weight greater than 3.5 kDa, and not in the dialysis diffusate which was the fraction containing components of molecular weight lower than 3.5 kDa. The phagocytosis-inhibiting activity was found to be mostly in the fraction which was seen as the first peak on the elution trace (Fraction 8), which was eluted at a volume which was greater than the void volume of the column. A small amount of activity was found to be in the fraction which was seen as the following peak on the elution trace. The fraction of manuka honey in the first and second peaks eluted from the column of Superose 12 were then run on SDS-PAGE (polyacrylamide gel electrophoresis with sodium dodecyl sulphate present). Silver-staining showed one band to be present. The corresponding part of the gel was excised from an unstained part of the gel and the protein was digested with trypsin and the peptides thus obtained were run on MALDI-TOF MS (matrix-assisted laser desorption time of flight mass spectrometry). The mass of the peptides was compared with data in the Swiss-Prot database and was found to match with Major Royal Jelly Protein-1 (also known as Apalbumin-1) for the protein in the first peak from Superose 12 chromatography, and with Major Royal Jelly Protein-3 (also known as Apalbumin-3) for the protein in the first peak from Superose 12 chromatography.

Figure 2:
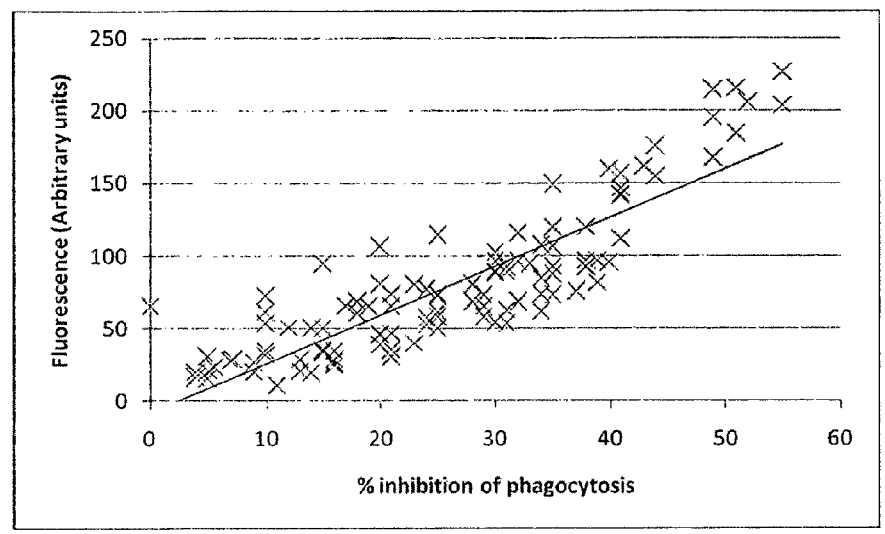
FIG. 2 depicts a graph of phagocytosis inhibition (PIA) versus fluorescence for a number of honey samples.
Figure 8:
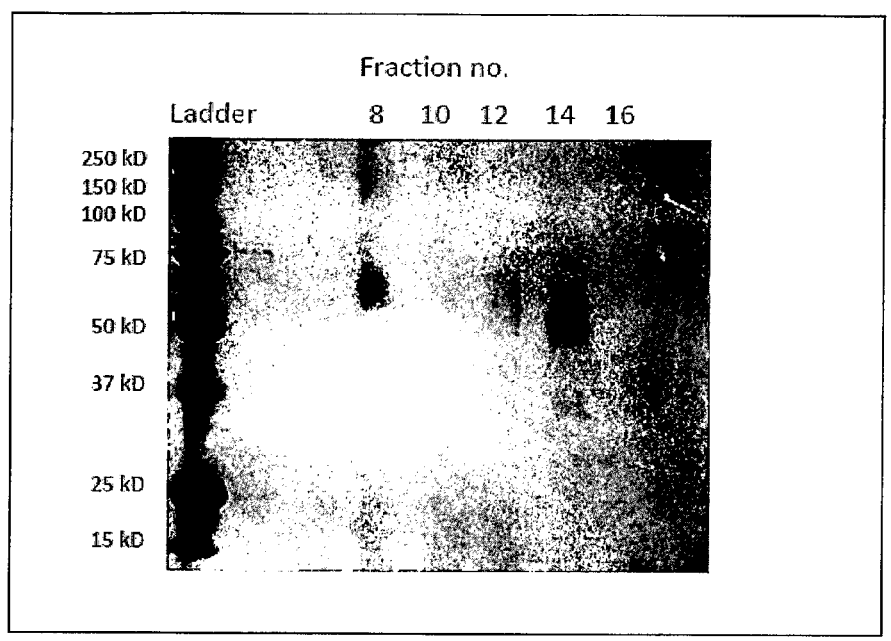
FIG. 8 shows the image of a silver-stained SDS electrophoresis gel run with fractions from the Superose 12 chromatography column.

Having found by activity-led fractionation that an Apa1 or a MRJP-1 protein was the component responsible for the anti-inflammatory activity, and knowing that other honeys have the presence of Major Royal Jelly Proteins further work was conducted to determine if the presence of the high levels of MGO in the manuka honey was modifying the Apa1/MJRP protein. It was found that Manuka honey had a high fluorescence that was not seen in other honey types to the same extent and that this fluorescence was due to MGO modifying the proteins in honey. Without wanting to be bound to any particular theory the high level of MGO that is a unique feature of manuka honey is thought to cause glycation of the Apa1/MRJP protein to form Advanced Glycation End-products (AGEs) which are fluorescent as reported in Schmitt et al, *Analytical Biochemistry*, 2005. It was found by the inventors that the incubation of honey with MGO, gave rise to an increase in fluorescence, at the same emission wavelength as the fluorescence developed in bovine serum albumin when it was incubated with MGO. Further analysis showed that anti-inflammatory activity also increased as a result of this treatment. A correlation was found between the fluorescence and the anti-inflammatory activity of samples of honey as shown in FIG. 2. The treatment with MGO also increased the molecular weight of the Apa1/MRJP protein (on SDS electrophoresis), the band of increased molecular weight being fluorescent as shown in FIGS. 8 and 10.

Methods of Use for MGO Modified Apalbumins

Inflammation in tissue may be reduced by administering one or more purified MGO-modified Apalbumin polypeptides or a MGO-modified Apalbumin-containing composition to inflamed tissue.

MGO-modified Apalbumin reduces inflammation in tissue by reducing the rate of phagocytosis by immune cells, and by blocking the mannose receptors on immune cells, which trigger phagocytosis. Immune cells include macrophages, monocytes, dendritic cells, and granulocytes.

MGO-modified Apalbumin may be administered to inflamed tissue in various different forms, including MGO-modified Apalbumin which has been purified from other components, and MGO-modified Apalbumin which is in a composition containing one or more other types of compounds such as pharmaceutically acceptable carriers, adjuvants, or therapeutic molecules. MGO-modified apalbumin may be purified from active manuka honey, or from manuka honey or any other type of honey to which MGO or an MGO precursor has been added to modify the apalbumin, or it may be purified from royal jelly or a system in which apalbumin is recombinantly expressed and then treated with MGO.

MGO-modified apalbumin in a composition containing one or more other types of compounds includes MGO-modified apalbumin in honey or a honey extract that has been enriched for MGO-modified apalbumin, MGO-modified apalbumin in extracts related to the recombinant production of apalbumin and the chemical modification of apalbumin with MGO.

Purified MGO-modified apalbumin or MGO-modified Apalbumin 1-containing compositions may be administered to inflamed tissue in various different forms, including but not limited to: creams, lotions, liquid solutions, or poultices. MGO-modified Apalbumin may also be administered to inflamed tissue as by inclusion of MGO-modified Apalbumin in an edible product. Such products include but are not limited to: beverages, candies, syrups, lozenges, pills, and foods.

Methods of Detecting MGO-Modified Apalbumin and Characterizing Properties of Honey The anti-inflammatory capacity of a sample of honey may be determined through detection of a MGO-modified Apalbumin. The chemical modification of Apa1 by MGO generates MGO-modified Apa1 that exhibits greater fluorescence than Apa1 that has not been modified by MGO. Because Apa1 is present in honey, by measuring the fluorescence of a sample of honey, a measurement of the relative concentration of MGO-modified Apa1 in the honey sample can be obtained. A measurement of the concentration of MGO-modified Apa1 in a sample of honey directly relates to the anti-inflammatory capacity of the sample of honey. FIG. 2 depicts the correlation between fluorescence, and thus MGO-modified Apa1 content, and phagocytic inhibition capacity.

By measuring the fluorescence of samples of honey with known low concentrations of MGO-modified Apalbumin, such as Apa1, and also the fluorescence of samples of honey with known high concentrations of MGO-modified Apa1, a standard scale can be generated, which correlates the fluorescence of a sample of honey to the concentration of MGO-modified Apa1 in that sample of honey. In order to obtain samples of honey that contain a known MGO-modified Apa1 concentration that can be used for fluorescence testing and standard scale generation, the MGO-modified Apa1 concentration of samples of honey can be determined by standard analytical chemistry techniques, such as mass spectroscopy.

Once a standard scale is generated that correlates the fluorescence of a sample of honey with the MGO-modified Apa1 concentration in the sample of honey, that standard scale may be used in combination with fluorescence testing of samples of honey in order to generate various types of information useful for honey production and analysis.

For example, the fluorescence of a sample of honey with unknown MGO-modified Apa1 concentration can be measured, and based upon the fluorescence measurement and the standard scale, the concentration of MGO-modified Apa1 in the test honey sample can be determined. This fluorescence method of determining the concentration of MGO-modified Apa1 in a sample of honey is much cheaper and faster than other analytical chemistry techniques, such as mass spectroscopy. By measuring the concentration of MGO-modified Apa1 in the honey sample in this way, the anti-inflammatory capacity of the honey sample is also quickly determined.

Because high MGO concentration is a feature unique to manuka honey among all honey varieties, honey producers may try to simulate active manuka honey by adding MGO to samples of honey that do not naturally contain a desired concentration of MGO. Consumers prefer naturally occurring honeys over treated honeys. Purified, active MGO is readily available from commercial chemical producers (e.g. Sigma-Aldrich, St. Louis, Mo., sells a solution of 40% methylglyoxal in water), and honey producers may add MGO to a sample of honey that does not naturally contain a desired concentration of MGO, in order to raise the concentration of MGO in the honey sample to a desired level. A "process independent from natural honey formation" includes any activity not performed by bees, and it therefore includes activities such as addition of purified MGO to a honey sample. A "process independent from natural honey formation" does not include activities such as bees collecting nectars, pollens, or other plant products that contain high levels of MGO or MGO-precursor molecules.

The fluorescence of honey may also be used to determine an appropriate time to harvest honey from a hive or to store harvested honey in order to obtain honey with desired anti-inflammatory properties. Because the modification of apalbumin by MGO in honey may occur over a period of time, a honey producer may choose to keep honey in the hive until it contains a desired anti-inflammatory capacity and concentration of MGO-modified apalbumin. By measuring the fluorescence of samples of honey from the hive at different time intervals, a honey producer can use the measurement of the fluorescence of the honey as a method for determining the optimal time to harvest honey from the hive in order to obtain a honey having desired anti-inflammatory properties in the honey. Similarly, a honey producer may also measure the fluorescence of honey stored outside of the hive, in order to determine if the honey sample has a desired level of anti-inflammatory properties. By measuring the fluorescence of honey samples, a honey producer seeking to obtain a honey sample containing a desired anti-inflammatory capacity can store honey until it has developed a desired level of anti-inflammatory capacity by the formation of MGO-modified apalbumin.

Modification of Royal Jelly with MGO and Assessment of the Resulting Molecular Weight Changes.

Royal jelly was taken and analysed by MALDI-TOF using sinipanic acid as the matrix and in positive ion mode. One significant peak at approximately m/z of 52.4 kDa was identified. This peak corresponded with the m/z of 52.4 kDa obtained from a reverse phase isolated fraction that had previously been identified as major royal jelly protein.

The analytical RP HPLC protocol was performed on a Phenomenex Proteo90 column (3μ, 90 Å, C18, 250×4.06 mm) with a Phenomenex SecurityGuard C-18 guard column. The column was equilibrated with Buffer A: 0.1% TFA in Nanopure water, flow rate 1 mL/min. A gradient of buffer B (100% acetonitrile containing 0.1% TFA) was applied as follows and the absorbance was monitored at 214 nm (Table 1).

The royal jelly was then reacted with methylglyoxal at 0.1%, 0.5% and 1.0%. The royal jelly protein solutions were prepared by dissolving the partly defrosted preparation in PBS at a concentration of 10 mg/mL. MGO solutions were prepared by diluting the stock solution (Sigma, 40%) with PBS to obtain end concentrations in the range of 0.1, 0.5 and 1.0%. To 900 μL of the protein solution 100 μL of MGO solution of the required concentration was added and the mixture was incubated overnight at 60° C. The resulting reaction product was also studied by MALDI TOF MS. Using MALDI TOF MS only one significant peak was seen in the 0.5 and 1.0% MGO reaction products, that being the modified MRJP1 major protein at approximately 55.1 kDa. In the 0.1% MGO reaction it was clear from the MALDI-TOF spectra that there was not only the presence of underivatised protein, but also the modified MRJP-1 major protein. This suggested that the level of MGO was not sufficient to complete the reaction with MRJP-1 The shift in the m/z from 52.4 kDa to 55.1 kDa can be accounted for based on the addition of a single MGO unit accounting for an 72.07 Da adduct on Arg to produce methylglyoxal-derived dihydroxyimidazolidine (MG DH), and a mass shift of 70.05 for methylglyoxal-derived hydroimidazolone (MG-HI). Reaction with lysine to form CEL with a mass shift of 72.07 for CEL, Nε-(carboxymethyl)lysine and 180.25 Da increase for MOLD MOLD, methylglyoxal lysine dimmer. Other arginine modifications and their mass changes are 2-ammonio-6-([2-[(4-ammonio-5-oxido-5-oxopentyl)amino]-4-methyl-4,5-dihydro-1H-imidazol-5-ylidene]amino)hexanoate (MODIC) an increase of 166.23 Da, tetrahydropyrimidine (THP) which has a mass change of 160.18 Da and argpyrimidine with a mass change of 80.09. See Brock et al.—Detection and identification of arginine modifications on methylglyoxal-modified ribonuclease by mass spectrometric analysis in *J. Mass Spectrom.* 2007; 42: 89-100 Published online 4 Dec. 2006 in Wiley InterScience.

Table 3 of the Molecular Weight changes associated with MGO modifications

| MGO modification | Mass change |
| --- | --- |
| MGDH | 72.07 |
| MGHI | 70.05 |
| CEL | 72.07 |
| MOLD | 180.25 |
| MODIC | 166.23 |
| THP | 160.18 |
| argpyrimidine | 80.09 |

Figure 11:
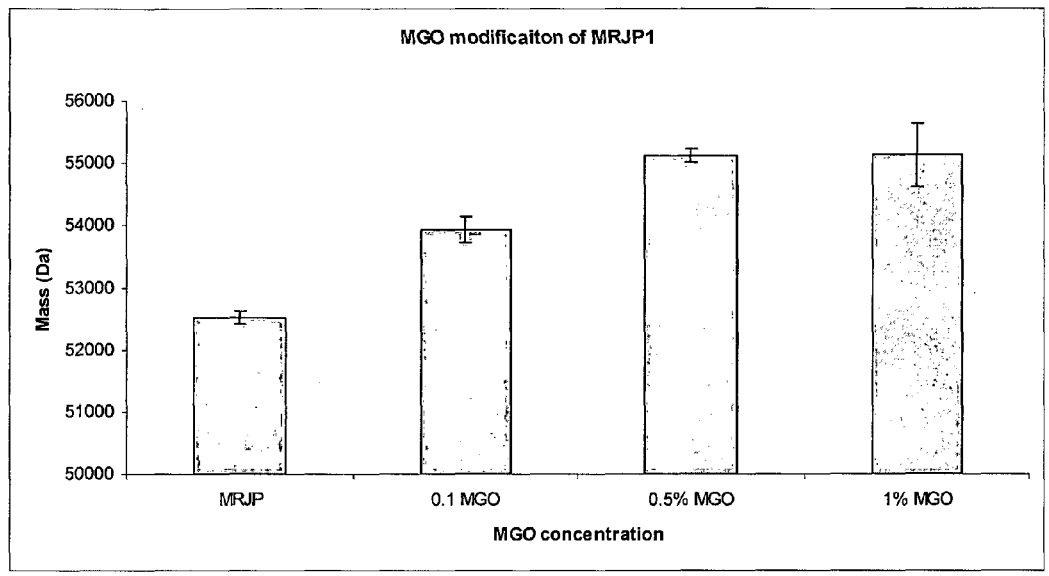
FIG. 11 shows the mass change in daltons brought about by MGO modification to MRJP1 at varying concentrations of MGO.
Figure 12:
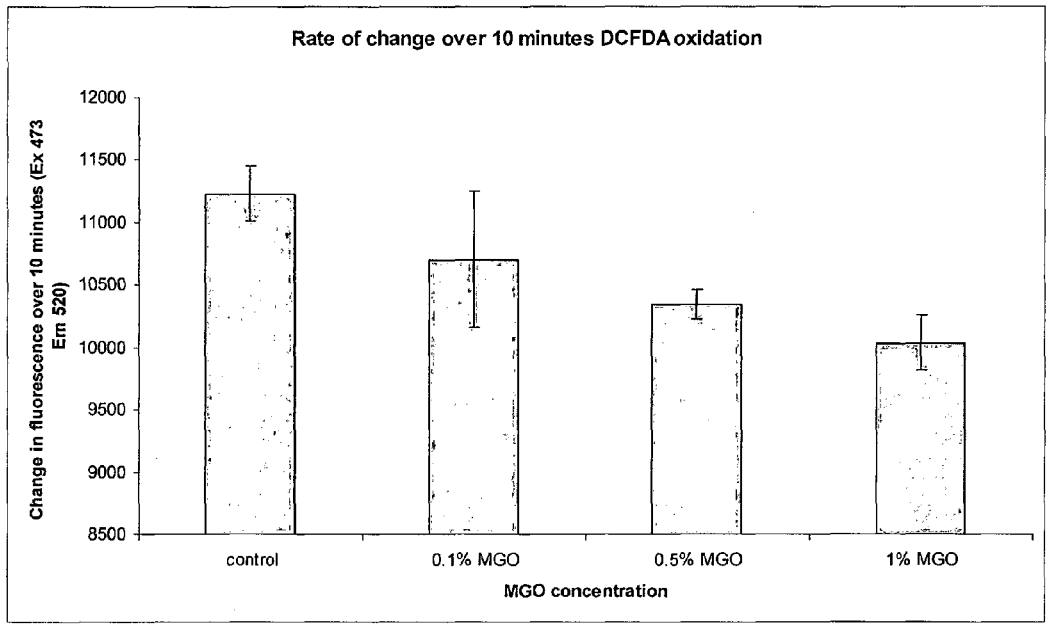
FIG. 12 shows the DFCDA biological assay results achieved by MGO modification to MRJP1 at varying concentrations of MGO.

As a number of adducts are possible and the likelihood for each forming varies an average number of 82 was used to determine the relative levels of MGO modification on MRJP1. In the case of 0.1% MGO that resulted in a partially reacted MRJP1 protein the difference in mass units compared with the unreacted MRJP1 was 1422.0 Da, being approximately 17 MGO adducts formed on the MRJP1. In the case of 0.5% and 1.0% MGO reaction products the differences in mass units can be seen in the Table 4 below. Both 0.5% and 1.0% MGO gave approximately 31-32 MGO adducts being formed on the MRJP1. It is also notable that there are a maximum of 39 sites that MGO can form an adduct on the MRJP1 (excluding Cys residues). There are 22 arginine sites and 17 lysine sites. What the results suggest is that approximately 82% of the possible sites for MGO adduct formation are being modified by MGO. Because both 0.5% and 1.0% MGO reacted substantially equivalently with MRJP1, as represented in FIG. 11, it is possible to conclude that the reaction had proceeded to completion. Furthermore it is notable that the natural levels of MGO in manuka honey tend to accumulate to approximately 0.4 to 0.5%. It was then further established by the DCFDA assay (detailed below) that the biological activity of the 0.5% and 1% MGO reaction products was statistically significant over the control, whereas the 0.1% MGO reaction products were not—see FIG. 12. This suggests that at least 17 MGO site modifications need to be present to see activity in the modified MRJP1 reaction product.

TABLE 4

| | MRJP1 alone | MRJP1 and 0.1% MGO | MRJP1 and 0.5% MGO | MRJP1 and 1.0% MGO |
| --- | --- | --- | --- | --- |
| Difference in Molecular Weight with MGO modification (mass units) | 0 | 1422.0 | 2589.8 | 2605.1 |
| Number of MGO modifications based on the addition of an 82 dalton adduct) | 0 | 17.3 | 31.6 | 31.8 |

DCFDA ROS Activity Assay

Figure 13:
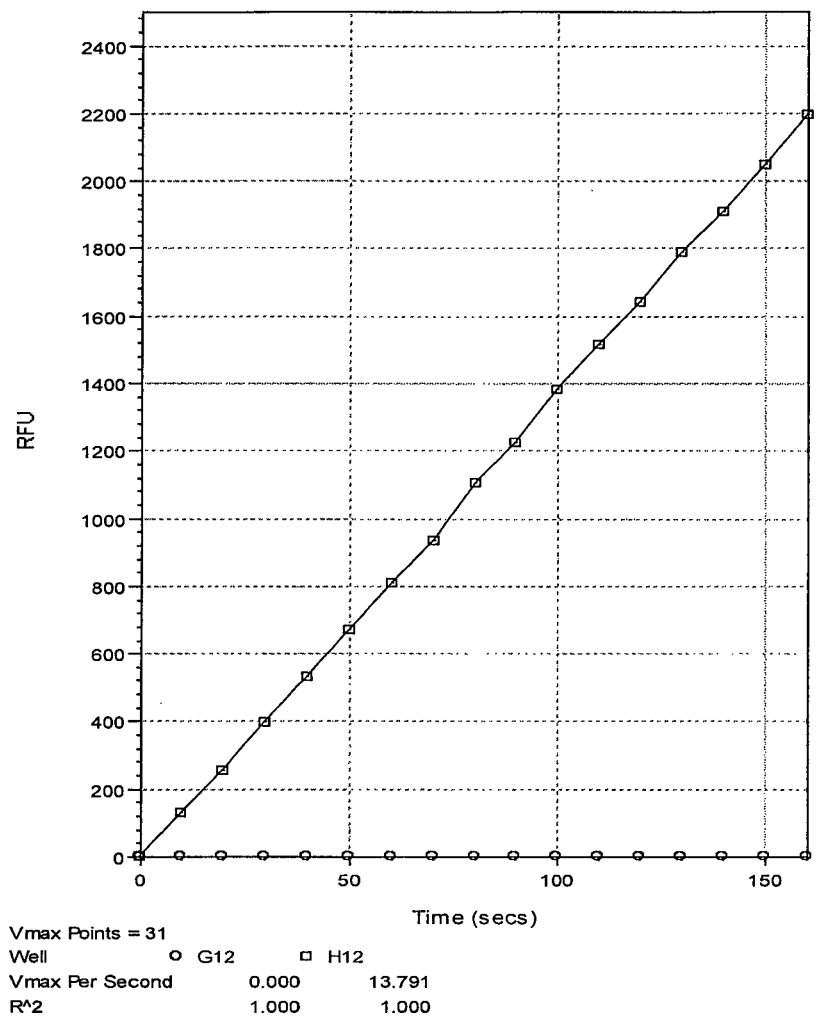
FIG. 13 shows a plot of the kinetic analysis of the DCFDA assay using 10 µL of cells.

Cells constantly generate reactive oxygen species (ROS) during aerobic metabolism. The ROS generation plays an important protective and functional role in the immune system. Cells are armed with a powerful antioxidant defense system to combat excessive production of ROS. Oxidative stress occurs in cells when the generation of ROS overwhelms the cells' natural antioxidant defenses. ROS and the oxidative damage are thought to play an important role in many human diseases including cancer, atherosclerosis, other neurodegenerative diseases and diabetes. Thus, establishing their precise role requires the ability to measure ROS accurately and the oxidative damage that they cause. There are many methods for measuring free radical production in cells. ROS production leads essentially to an inflammatory response. The most straightforward techniques use cell permeable fluorescent and chemiluminescent probes. 2'-7'-Dichlorodihydrofluorescein diacetate (DCFDA) oxidation is one of the most widely used techniques for directly measuring the redox state of a cell. It has several advantages over other techniques developed. It is very easy to use, extremely sensitive to changes in the redox state of a cell, inexpensive and can be used to follow changes in ROS over time. The DCFDA assay for reactive oxygen species ROS production, an indicative measure of an inflammatory response in cells, was developed as an alternative biological activity test to the phagocytosis test described above. The assay was prepared by placing 90 µL of phosphate buffered saline (PBS) and 10 µL of cells along with the sample of interest into 96 well plate in triplicate followed by the addition of 50 µL of DCFDA solution. DCFDA was prepared by dissolving 3 mg in 1 mL of DMSO. Then 100 µL of the DMSO solution was mixed with 10 mL of PBS. The oxidation of DCFDA into fluorescein was monitored using fluorescence in a Spectra-Max M4 plate reader using Ex 473 nm and Em 520 nm. Assays were monitored at time 0 min, 2 min, 5 min and 10 minutes. An initial assay was performed using kinetic analysis where measurements were made every 10 s for a period of 5 minutes in the presence and absence of cells. The initial plates were used to determine how many cells were needed and what volume of sample to use. The standard error of the mean across the entire 96 well plate was only 5%. By using a multi channel pipette we were able to confidently do an entire plate of analysis within 10 minutes. This rapid turnaround was necessary to analyze the samples generated and undertake assay guided fractionation of the samples in order to attempt to identify the proteins and peptides of interest. Kinetic analysis of the DCFDA assay using 10 µL of cells is shown in FIG. 13.

Activation of the ovine spleen cells with LPS and 1 µm spheres did not appear to be necessary as the samples were prepared without the use of sterile techniques and used immediately. As shown by FIG. 1 a linear oxidation of DCFDA was obtained in the presence of cells only and DCFDA appeared to be stable to the conditions used.

Preparation of Cells for the DCFDA ROS Activity Assay

Whole fresh spleens were obtained from a local abattoir (Taylor Preston Wellington). Cells were typically obtained within 1 hour of collection but processing of spleen cells after 24 hour of storage at 4° C. was also performed. A spleen was sliced longitudinally with 1 cm gaps between the incisions and then a gel knife was used to scrape the red cell mass out of the spleen. The cells were mixed with 200 mL of PBS and then briefly homogenized with a hand blender to break up the cell mass into individual cells. The mixture was then poured through 4 layers of muslin cloth. The cells were then stored at 4° C. until used.

The Significance of the Lysine Residues

Acetylation selectively blocks the lysine residues. 1.2814 g of defrosted RJP mixture was dissolved in 50 mL of Tris/HCl (0.1 M, pH 8.5) containing 6 M urea. The solution was cooled down on an ice water bath. Acetic anhydride was added every 20 minutes in aliquots of 0.5 ml over a period of 2 hours. The pH of the solution was determined before every addition and adjusted to a pH above 7.5 using Tris/HCl buffer (1 M, pH 8.5). Then the sample was transferred to a dialysis tubing (molecular weight cut off 10 kDa) and dialysed over night against 1.6 liters of water with three changes of dialysate. The content of the dialysis tubing was frozen and freeze dried. 239.9 mg of a white slightly sticky material was recovered. The acetylated sample was found to no longer have activity in the DCFDA assay after MGO treatment. This indicated that the MGO modification of lysine residues is essential for the functional activity seen by modified MRJP.

Lys C Digestion:

a sample of royal jelly was hydrolyzed using the following protocol. 4 µg of Lys C was dissolved in 100 µL of ammonium carbonate pH 8.4. 10 µL of Lys C stock solution was added directly to 100 µg of MRJP extract in 100 µL. The reaction was performed for 72 hours at room temperature. The sample was then mixed 1:1 with Sinapinic acid solution and 1 µL spotted in duplicate on to MALDI TOF 384 well plate. Applied Biosystems Voyager 5800 was used to analyse the peptide to determine the masses and MSMS spectrum. The Lys C extracts from modification using MGO at 0.1, 0.5 and 1.0% were studied by mass spectrometry and the MS plots are shown in FIGS. 15 to 19. Larger peaks and more peaks were identified from the Lys C extracts after MGO modification of MRJP1. It was also observed that the higher the MGO concentration the greater number of larger peaks were observed. These Lys C results suggest that multiple modifications have occurred on various Lys residues across the MRJP1.

Trypsin spin column hydrolysis of MRJP1 and MGO modified MRJP1: a sample of royal jelly (10 mg/mL) was subjected to trypsin hydrolysis using Sigma trypsin spin column (TT0010) using manufactures instructions. The hydrolysis was performed for 30 minutes at room temperature with two passes of the MRJP (100 µg) in ammonium bicarbonate buffer. MRJP were also reacted with MGO at 0.1, 0.5 and 1.0% concentration overnight at 60° C. The MGO modified MRJP were also subjected to trypsin hydrolysis under identical conditions as that described for the native enzyme. The MGO modified MRJP samples were also tested for their ability to reduce the oxidation rate of DCFDA. The two higher concentrations were shown to be highly active. A lower amount of activity was observed in the 0.1% MGO treated sample.

Figure 20:
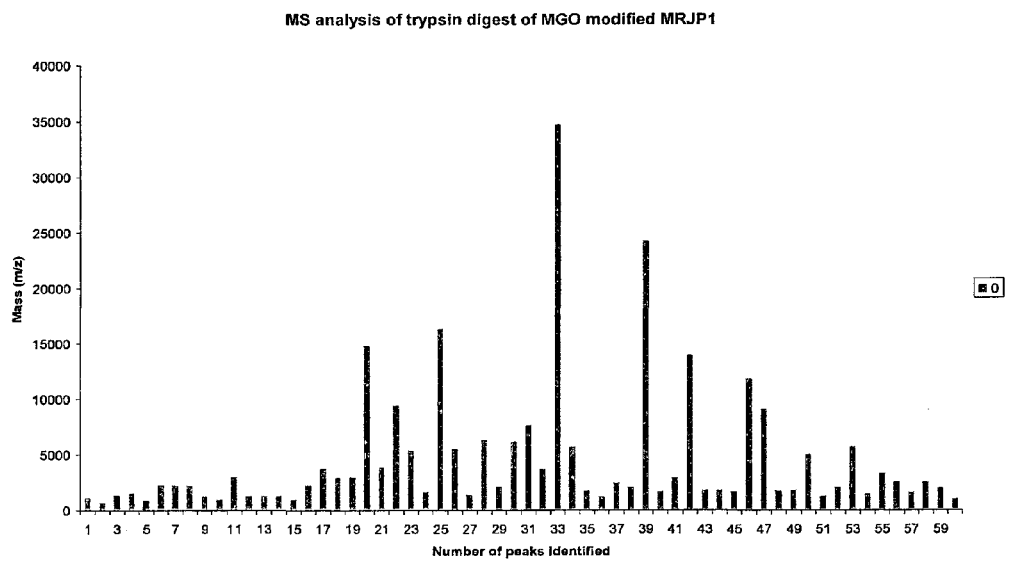
FIG. 20 shows Peaks identified as originating from MRJP1-trypsin digest of MRJP extract with no MGO modification.
Figure 21:
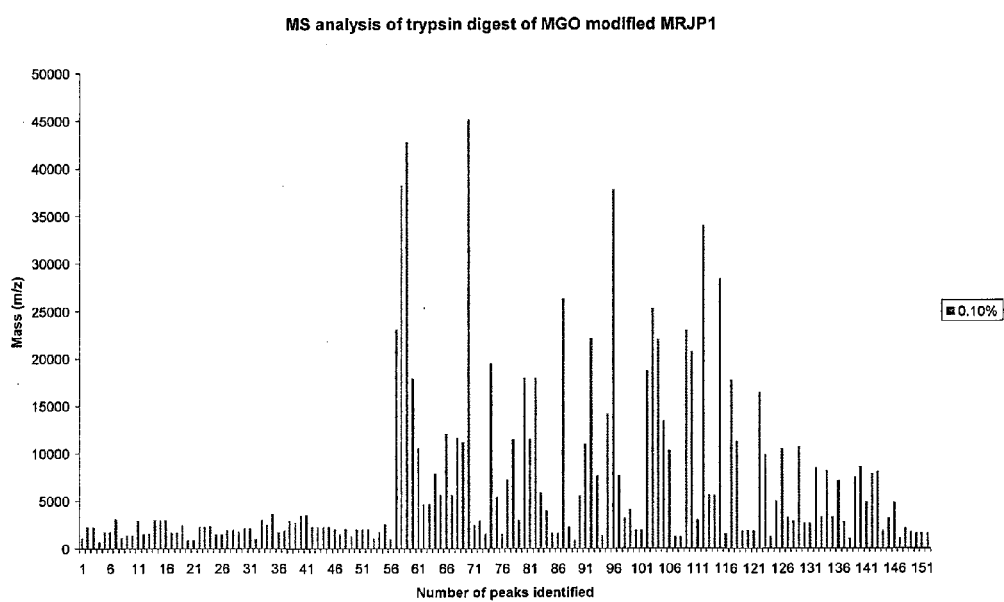
FIG. 21 shows Peaks identified as originating from MRJP1-trypsin digest of MRJP extract with 0.1% MGO modification.
Figure 22:
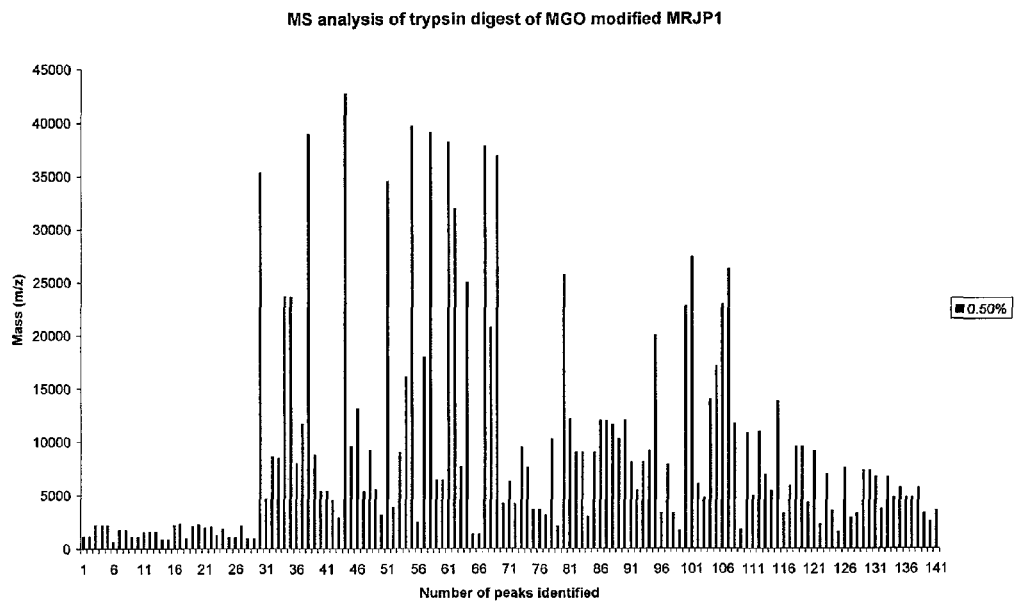
FIG. 22 shows the MS peaks identified as originating from MRJP1-trypsin digest of MRJP extract with 0.5% MGO modification
Figure 23:
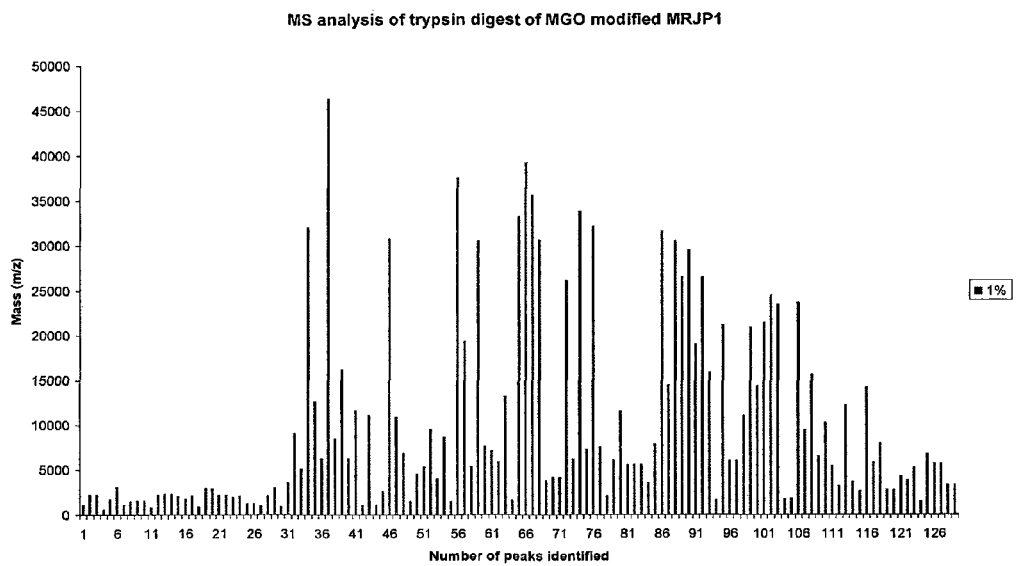
FIG. 23 shows the MS peaks identified as originating from MRJP1-trypsin digest of MRJP extract with 1% MGO modification

The modified MGO (0.1, 0.5 and 1.0%) trypsin digests were studied by mass spectrometry and the MS plots are shown in FIGS. 21 to 23. The unmodified trypsin digest MS plot is shown in FIG. 20. The sequence coverage for MRJP1 was extensive and many small fragments were detected when the protein was hydrolyzed in its native state. However, when MGO modification occurs at various Lys and Arg residues on MRJP1 up to six different adducts can form and the number of combinations generated based on the positional locations of the adducts generates many more peptides. The modification also blocks the cleavage site for trypsin so this reduces the potential number of peptides generated. What is observed is a greater number of larger peptides as certain sites are prevented from being cleaved through modification of the Lys and Arg residues. A greater number of peptides were observed for the MGO treated MRJP1. This is in agreement with the expected random reactivity of the Lys and Arg residues and the likelihood for the generation of multiple adducts of varying positions providing the active material of interest.

Hydrolysis of MRJP extracts were performed with various enzymes including trypsin and MGO modification of the digests was undertaken. The resulting hydrolyzed extracts were found to have good activity in the DCFDA assay (results not shown).

Modification of Untreated RJP with Alternative Reagents

A number of other compounds that cross link proteins were also investigated including glyoxal and glutaraldehyde to determine if a similar level of anti phagocytotic activity could be generated using these agents.

Untreated MRJP was treated with other reagents which are known to cross link peptides and proteins. These included glyoxal, glutaraldehyde and formaldehyde. A solution of glyoxal was made up to a final concentration of 10 mg/mL using PBS. The stock solutions of glutaraldehyde (25%) and formaldehyde (37%) were diluted 2.5 and 3.7 times using PBS, respectively, to give final concentrations of 10%. 500 μl of these reagent solutions were added to 4.5 ml RJP solution (10 mg/mL) and incubated at 60° C. overnight.

Figure 14:
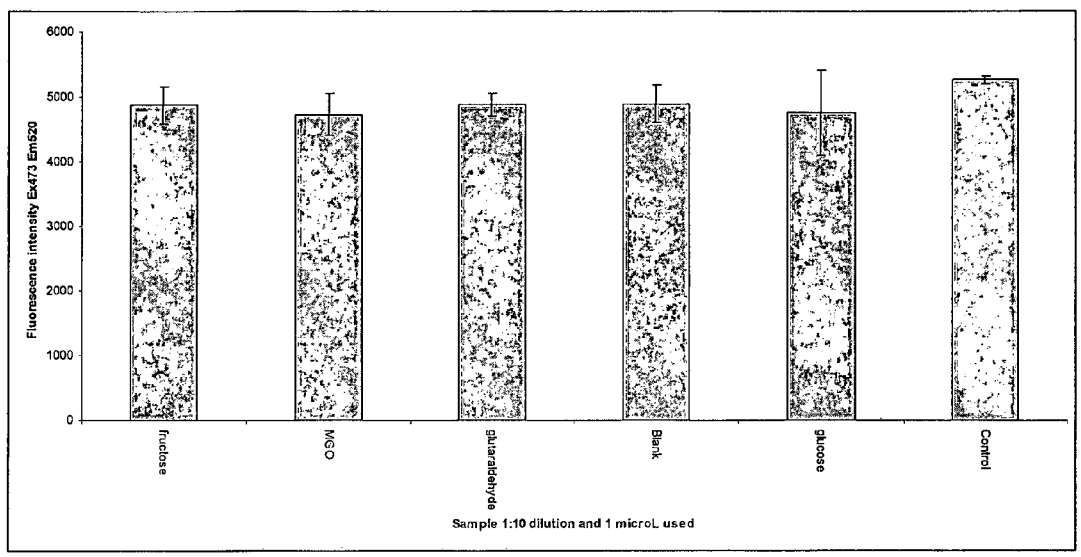
FIG. 14 shows the DFCDA biological assay results achieved by modification of MRJP1 using MGO, fructose, glutaraldehyde and glucose.
Figure 15:
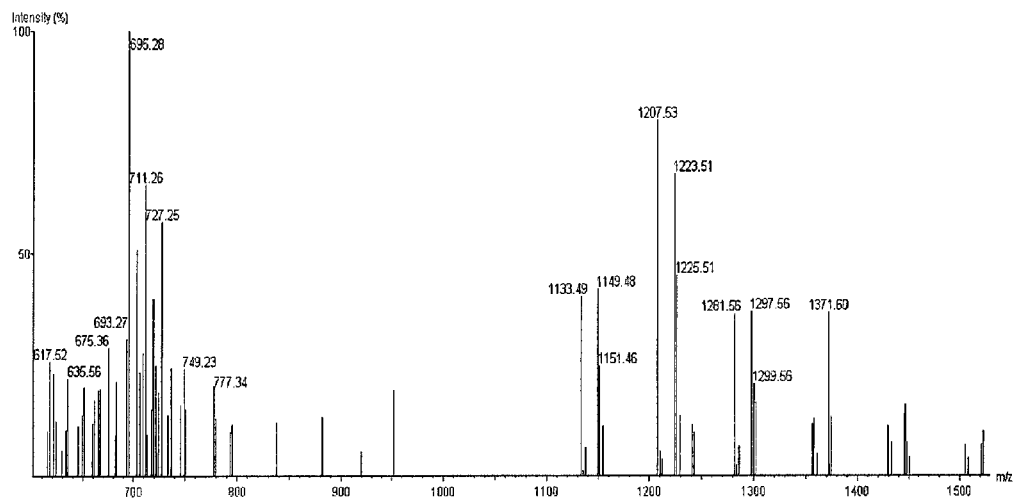
FIG. 15 shows the MS of a Lys C digestion of MRJP.
Figure 16:
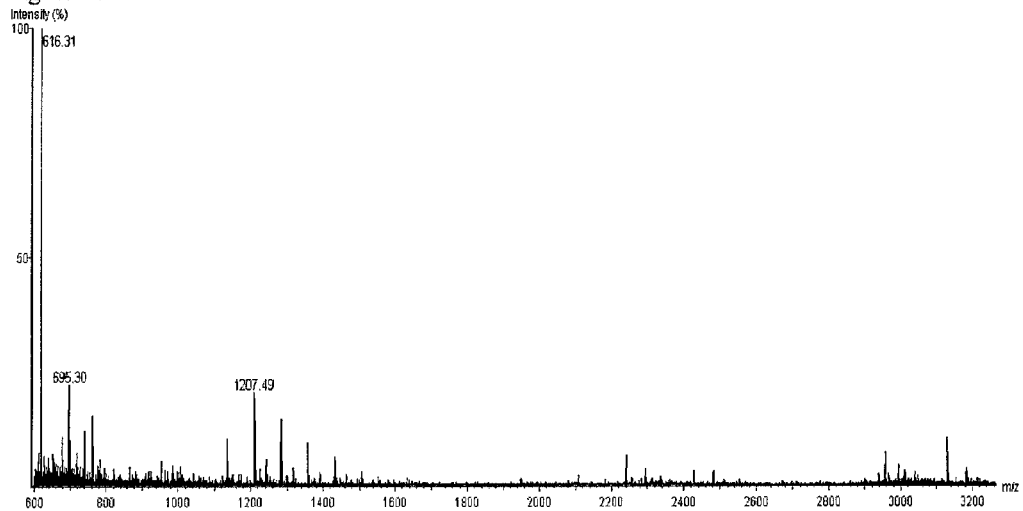
FIG. 16 shows the MS of a Lys C digestion of MRJP modified with 0.1% MGO.
Figure 17:
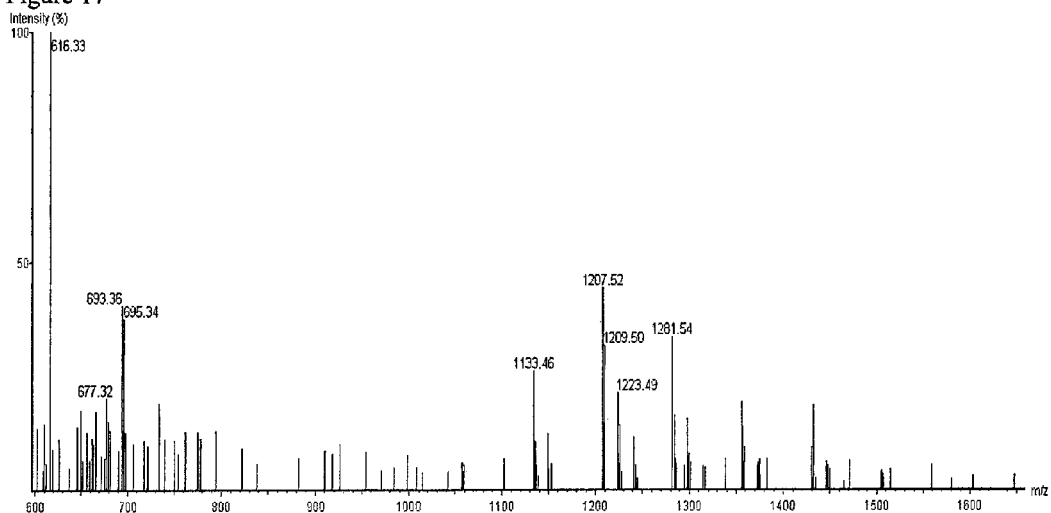
FIG. 17 shows the MS of a Lys C digestion of MRJP modified with 0.5% MGO
Figure 18:
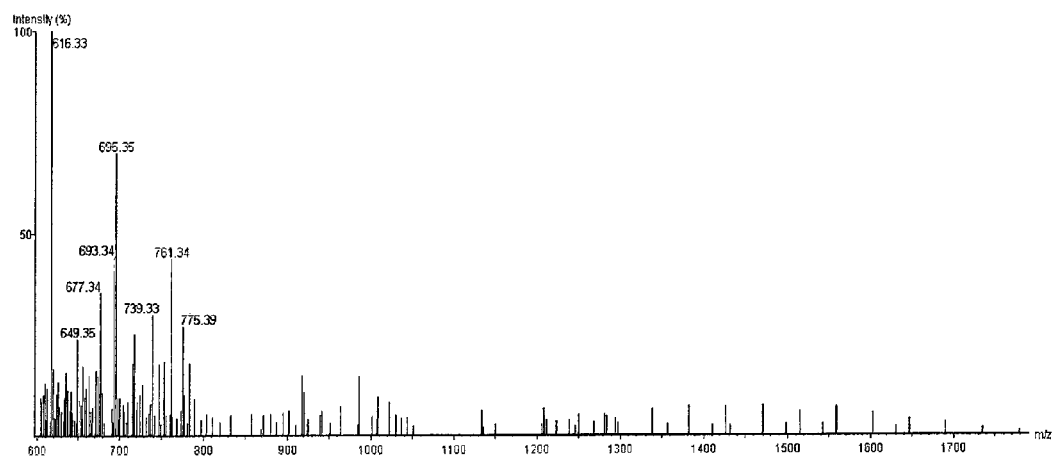
FIG. 18 shows the MS of a Lys C digestion of MRJP modified with 1.0% MGO.
Figure 19:
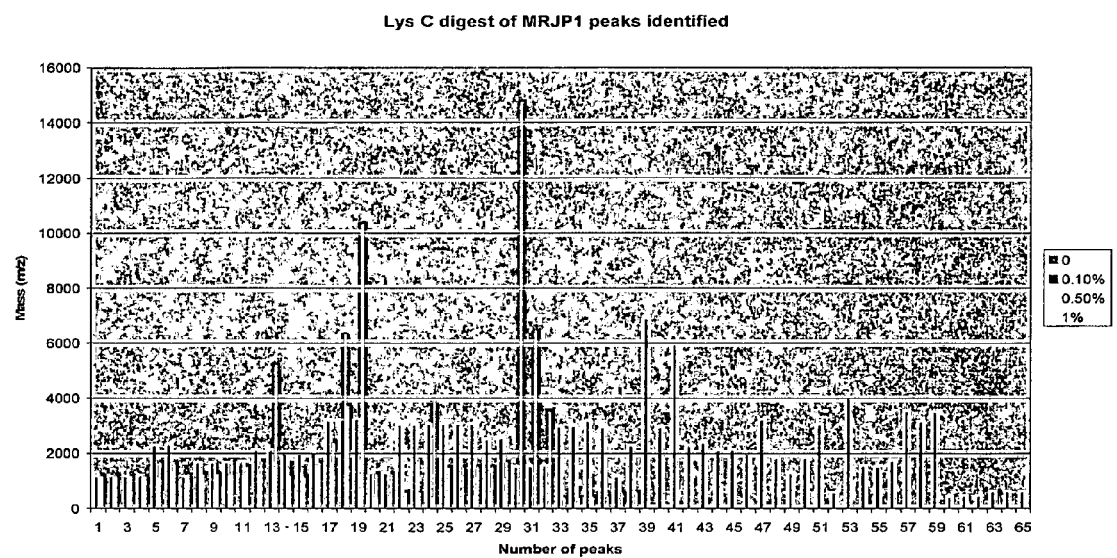
FIG. 19 shows an overlay of the MS plots of the Lys C digestions shown in FIGS. 15 to 19.

RJP was also reacted with glucose and fructose as follows. To 4.5 ml protein solution in PBS (10 mg/mL) 500 μL solution of the respective carbohydrate (10 mg/mL) in PBS were added and the mixture was incubated at 60° C. overnight. MRJP was prepared at 10 mg/mL in PBS and modified overnight at 60° C. with the following reagents: 1) glyoxal, 2) glucose (10% 2 mL 10 mg/mL 19.7+1.97), 3) fructose (10% 2 mL 10 mg/mL 24.1+2.41), 4) glutaraldehyde (25% diluted 2.5×2 mL 800 microL+12 mL of PBS), 5) MGO (40% diluted 4×2 mL 500 microL+1.5 mL PBS) and untreated Blank. The samples were tested in the DCFDA assay for ROS production and the results shown in FIG. 14. Statistically significant results were observed when MRJP were either modified with MGO or glutaraldehyde. No activity was seen when glucose or fructose were used as the cross linkers. This suggests that the anti phagocytosis activity is directly related to the ability to form a covalent bond a cross-link. This activity was observed with a 1:1000 dilution of the sample to counter any free MGO that may have been present in the initial sample The MALDI-TOF work described in this section was completed at the University of Victoria Mass Spectrometry Facility, Wellington, New Zealand.

The present invention and its embodiments have been described in detail. However, the scope of the present invention is not intended to be limited to the particular embodiments of any process, manufacture, composition of matter, compounds, means, methods, and/or steps described in the specification. Various modifications, substitutions, and variations can be made to the disclosed material without departing from the spirit and/or essential characteristics of the present invention. Accordingly, one of ordinary skill in the art will readily appreciate from the disclosure that later modifications, substitutions, and/or variations performing substantially the same function or achieving substantially the same result as embodiments described herein may be utilized according to such related embodiments of the present invention. Thus, the following claims are intended to encompass within their scope modifications, substitutions, and variations to processes, manufactures, compositions of matter, compounds, means, methods, and/or steps disclosed herein.

REFERENCES

K. Kohno, I. Okamoto, O, Sano, N. Arai, K. Iwaki, M. Ikeda, and M. Kurimoto, "Royal Jelly Inhibits the Production of Proinflammatory Cytokines by Activated Macrophages", *Biosci. Biotechnol. Biochem.*, 68 (1), 2004 pp. 138-145.

Kimura Y, Miyagi C, Kimura M, Nitoda T, Kawai N, Sugimoto H. "Structural features of N-glycans linked to royal jelly glycoproteins: structures of high-mannose type, hybrid type, and biantennary type glycans." *Biosci. Biotechnol. Biochem.*, 64(10) (2000) pp 2109-20.

J. Simuth, K. Bilikova, E. Kovacova, Z. Kuzmova, and W. Schroder, "Immunochemical approach to detection of adulteration in honey: physiologically active Royal Jelly protein stimulating TNF-alpha release is a regular component of honey"; *Journal of Agriculture and Food Chemistry*, 52(8), 2004; pp. 2154-8.

B. Lerrer, K. Zinger-Yosovich, B. Avrahami, and N. Gilboa-Garber, "Honey and royal jelly, like human milk, abrogate lectin-dependent infection-preceding *Pseudomonas aeruginosa* adhesion"; *ISME Journal*, 1, 2007; pp. 149-155.

E. Mavric, S. Wittmann, G. Barth, and T. Henle "Identification and quantification of methylglyoxal as the dominant antibacterial constituent of Manuka (*Leptospermum scoparium*) honeys from New Zealand"; *Mol. Nutr. Food Res.* 52, 2008.

Auwerx J. (1991). "The human leukemia cell line, THP-1: a multifaceted model for the study of monocyte-macrophage differentiation." *Experientia*. 47:22-31.

Wan, C. P., C. S. Park, et al. (1993). "A rapid and simple microfluorometric phagocytosis assay." *Journal of Immunological Methods* 162(1): 1-7.

Allen, K. L., P. C. Molan, et al. (1991). "A survey of the antibacterial activity of some New Zealand honeys." *Journal of Pharmacy and Pharmacology* 43(12): 817-22.

White, J. (1975). *Honey: a comprehensive survey*. London, Heinemann.

Schmitt, A., J. Schmitt, et al. (2005). "Characterization of advanced glycation end products for biochemical studies: side chain modifications and fluorescence characteristics." *Analytical Biochemistry* 338: 201-215.

Jonathan W. C. Brock, 1 William E. Cotham, 1 Suzanne R. Thorpe, 1 John W Baynes1 and Jennifer M. Ames2. (2007). Detection and identification of arginine modifications on methylglyoxal-modified ribonuclease by mass spectrometric analysis. *J Mass Spectrom*. 2007; 42: 89-100

What we claim is:

1. A method of identifying (i) anti-inflammatory capacity and (ii) MGO-modified apalbumin concentration of a honey sample, comprising the steps of:
  a) measuring the fluorescence level of the honey sample,
  b) determining the concentration of MGO-modified apalbumin (MMA) in the honey sample by:
    comparing the fluorescence level of the honey sample to a standard scale that correlates fluorescence level to MMA-concentration, or
    comparing the fluorescence level of the honey sample to fluorescence levels of one or more control samples of honey with known MMA-concentrations, and
  c) determining the phagocytosis inhibition (PI) activity the honey sample by:
    comparing the fluorescence level of the honey sample to a standard scale that correlates fluorescence value to PI-activity, or
    measuring the PI-activity of the honey sample, and comparing the PI activity of the honey sample to PI-activities of one or more control samples of honey with known PI-activities,
  wherein (b) identifies the concentration of the MGO-modified apalbumin in the honey sample and (c) identifies the anti-inflammatory capacity of the honey sample.

2. The method of claim 1 wherein the MGO-modified apalbumin is a modified apalbumin 1 protein (modified MRJP1).

3. The method of claim 1, wherein the honey sample is obtained from a hive.

4. The method of claim 1, wherein the honey sample is obtained from a stored honey.

5. The method of claim 1, wherein one or more of the control samples of honey are manuka honey.

6. The method of claim 1, wherein the fluorescence level is measured at an emission wavelength between 440-560 nm.

7. The method of claim 1, wherein steps (a)-(c) are repeated after an interval of time, and wherein an increase in the fluorescence level and PI activity after the time interval is indicative of an increase in the anti-inflammatory capacity of the honey sample.

8. The method of claim 4, wherein the stored honey has been incubated at 30-40° C.

9. The method of claim 4, wherein the stored honey has been chemically treated with MGO, glyoxal, glutaraldehyde or a combination thereof.

* * * * *